(12) United States Patent
Zeylikovich et al.

(10) Patent No.: US 6,437,867 B2
(45) Date of Patent: *Aug. 20, 2002

(54) PERFORMING SELECTED OPTICAL MEASUREMENTS WITH OPTICAL COHERENCE DOMAIN REFLECTOMETRY

(75) Inventors: Iosif Zeylikovich, Charlotte, NC (US); Robert R. Alfano, Bronx, NY (US)

(73) Assignee: The Research Foundation of the City University of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/772,340

(22) Filed: Jan. 29, 2001

Related U.S. Application Data

(63) Continuation of application No. 09/378,846, filed on Aug. 23, 1999, now abandoned, which is a continuation-in-part of application No. 08/984,879, filed on Dec. 4, 1997, now Pat. No. 5,943,133.

(60) Provisional application No. 60/033,220, filed on Dec. 4, 1996, and provisional application No. 60/042,489, filed on Apr. 2, 1997.

(51) Int. Cl.$^7$ ................................................. G01B 9/02
(52) U.S. Cl. ....................................... 356/497; 356/521
(58) Field of Search ................................ 356/497, 521, 356/496; 250/237 G

(56) References Cited

U.S. PATENT DOCUMENTS

| | | |
|---|---|---|
| 3,614,235 A | 10/1971 | Munnerlyn |
| 4,167,337 A | 9/1979 | Jäerisch et al. |
| 5,459,570 A | 10/1995 | Swanson et al. |
| 5,568,256 A | 10/1996 | Körner et al. |
| 5,574,560 A | 11/1996 | Franz et al. |
| 5,943,133 A | 8/1999 | Zeylikovich et al. |

FOREIGN PATENT DOCUMENTS

| | | |
|---|---|---|
| WO | PCT/US97/22274 | 6/1998 |

OTHER PUBLICATIONS

Gilerson, Alexander et al., "High speed grating–generated electronic coherence microscopy of biological tissue without moving part," *SPIE Conference on Coherence Domain Optical methods in biomedical Science and Clinical Applications III*, San Jose, CA, Jan. 1999, pp. 213–215, SPIE, Bellingham, WA.

(List continued on next page.)

*Primary Examiner*—Samuel A. Turner
(74) *Attorney, Agent, or Firm*—Lyon & Lyon LLP

(57) ABSTRACT

A system and method for performing selected optical measurements on a sample is provided utilizing an optical coherence domain reflectometer which includes a diffraction grating. A broad band light source produces light having a short coherence length. A beamsplitter splits the light into a signal beam and a reference beam. A reference mirror is disposed to receive the reference beam. A lens brings the signal beam to focus on the sample. A diffraction grating receives reflections from the sample and from the reference mirror, the reflections being incident on the diffraction grating with respect to said diffraction grating normal such that a positive diffraction order from one of the reflections and a negative diffraction order from the other one of the reflections and a negative diffraction order from the other one of the reflections propagate along a common path. A lens collects the diffracted order from the diffraction grating directed along the common path and brings the diffracted orders to focus on a detector, the detector producing an output of said positive and negative diffracted orders received. A computer processes the output from the detector. In other versions of the invention, reflections from the sample are not directed onto the diffraction grating but instead are combined with a diffracted order from reflections from the reference mirror.

54 Claims, 31 Drawing Sheets

OTHER PUBLICATIONS

Izatt, Joseph A. et al., "Optical coherence microscopy in scattering media," *Optics Letters,* Apr. 15, 1994, pp. 590–592, vol. 19, No. 8, Optical Society of America, New York, NY.

Swanson, E. A. et al. "In vivo retinal imagining by optical coherence tomography," *Optics Letters,* Nov. 1, 1993, pp. 1864–1866, vol. 18, No. 21, Optical Society of America, New York, Ny.

Swanson, E. A. et al., "High–speed optical coherence domain reflectometry," *Optics Letters,* Jan. 15, 1992, pp. 151–153, vol. 17, No. 2, Optical Society of America, New York, NY.

Tearney, G. J. et al., "Rapid acquisition of in vivo biological images by use of optical coherence tomography," *Optics Letters,* Sep. 1, 1996, pp. 1408–1410, vol. 21, No. 17, Optical Society of America, New York, NY.

Tearney, G. J. et al., "Scanning single–mode fiber optic catheter–endoscope for optical coherence tomography," *Optics Letters,* Apr. 1, 1996, pp. 543–545, vol. 21, No. 7, Optical Society of America, New York, NY.

Youngquist, Robert C. et al., "Optical coherence–domain reflectometry: a new optical evaluation technique," *Optics Letters,* Mar. 1987, pp. 158–160, vol. 12, No. 3, Optical Society of America, New York, NY.

Zeylikovich, I. and Alfano, R.R., "Heterodyne grating–generated scan correlation interferometry for reflectometry and signal–processing applications," *Optics Letters,* Aug. 15, 1997, pp. 1259–1261, vol. 22, No. 16, Optical Society of America, New York, NY.

Zeylikovich, I. and Alfano, R.R., "Three–exposure interferometric histological imae reconstruction of biological tissue," *Proceedings of Optical Biopsy II,* Jan. 25–26, 1998, pp. 190–195, vol. 3250, SPIE, Bellingham, WA.

Zeylikovich, I. and Alfano, R.R., "Ultrafast correlation interferometric imaging through a moving scattering medium," *Optics Communications,* Feb. 15, 1997, pp. 217–222, vol. 135, Elsevier Science B.V.

Zeylikovich, I. and Alfano, R. R., "Ultrafast dark–field interferometric microscopic reflectometry," *Optics Letters,* Oct. 15, 1996, pp. 1682–1684, vol. 21, No. 20, Optical Society of America, New York, NY.

Zeylikovich, I. et al., "Interferometric 2D imaging amplitude correlator for ultrashort pulses," *Optics Communications,* Apr. 1, 1995, pp. 485–490, vol. 115, Elsevier Science B.V.

Zeylikovich, I. et al., "Nonmechanical grating–generated scanning coherence microscopy," *Optics Letters,* Dec. 1, 1998, pp. 1797–1799, vol. 23, No. 23, Optical Society of America, New York, NY.

Zeylikovich, I. et al., "Observation of light diffraction by time–resolved femtosecond correlation interferometry," *Optics Letters,* Jul. 15, 1995, pp. 1580–1582, vol. 20, No. 14, Optical Society of America, New York, NY.

CROSS-CORRELATION

PERFORMING SELECTED OPTICAL MEASUREMENTS WITH OPTICAL COHERENCE DOMAIN REFLECTOMETRY

CROSS-REFERENCE TO RELATED APPLICATIONS

This application is a continuation of U.S. patent application Ser. No. 09/378,846 filed on Aug. 23, 1999, which is a continuation-in-part of U.S. patent application Ser. No. 08/984,879 filed on Dec. 4, 1997 (now U.S. Pat. No. 5,943,133), which claims the benefit of U.S. provisional patent application No. 60/033,220 filed on Dec. 4, 1996, and U.S. provisional patent application No. 60/042,489 filed on Apr. 2, 1997, all of which patent applications are incorporated herein by reference.

BACKGROUND OF THE INVENTION

The present invention relates generally to a method and system for making optical measurements and, more particularly, to a method and system for making optical measurements using optical coherence domain reflectometry.

Optical coherence domain reflectometry (OCDR), a well-known technique, is based on detection of an interference signal and becomes an attractive method for making precision measurements that provide resolution of 10 $\mu$m and a dynamic range of more than 100 dB for depth scan up to few mm. Using a high speed linear translation stage, OCDR measurements can be performed at modest high speeds. This method can be used to determine an internal depth image below the surface. OCDR has been developed for imaging of the anterior eye and retina, optical tomography and histology in highly-scattering media, and catheter-endoscope tomography in internal organ systems. The mirror velocity is typically in the range of 30 mm/sec corresponding to a Doppler frequency of 50 kHz. To achieve ultrahigh image acquisition speeds alternative technologies to mirror-translation scanning must be developed.

In U.S. Pat. No. 4,459,570 issued on Oct. 17, 1995 to E. A. Swanson et. al, a method and apparatus for performing various optical measurements is provided utilizing an optical coherence domain refractometer (OCDR). A short coherence optical radiation source applies optical radiation through like optical paths to a sample and an optical reflector. The optical reflector is movable in accordance with a predetermined velocity profile to permit interferometric scanning of the sample, the resulting output having a Doppler shift frequency modulation. This output may be demodulated and detected to obtain desired measurements and other information. Additional information may be obtained by applying radiation from two or more sources at different wavelengths to the sample and reflector and by separately demodulating the resulting outputs before processing. Birefringent information may be obtained by polarizing the optical radiation used, by suitably modifying the polarization in the sample and reference paths and by dividing the output into orthogonal polarization outputs which are separately demodulated before processing.

Another reference of interest is U.S. Pat. No. 5,491,552 issued on Feb. 13, 1996 to A. Knuttel.

It is an object of this invention to provide a new and improved method and system for optically performing high resolution measurements.

It is another object of this invention to provide a new and improved method and system for optically performing high resolution measurements using a diffraction grating.

It is another object of this invention to provide a method and system for obtaining a 2D image of a sample without scanning the sample in the lateral direction.

It is a further object of this invention to provide a method and system for obtaining a 3D image of a sample.

SUMMARY OF THE INVENTION

A system for performing selected optical measurements on a sample constructed according to the teachings of certain embodiments of this invention comprises a broad band light source, a beamsplitter for splitting light from said broad band light source into a signal beam and a reference beam, a reference mirror disposed along the path of the reference beam, the sample being disposed along the path of the signal beam, a first lens for bringing the signal beam to focus on said sample, a diffraction grating for receiving reflections from the sample and from the reference mirror and producing therefrom a diffracted beam, the reflections from the sample and the reference mirror being incident on the diffraction grating such that a positive diffraction order from the reflections from one of the sample and reference mirror and a negative diffraction order from the reflections form the other one of the sample and reference mirror are directed along the same path, the number of the two diffraction orders being the same, i.e. both first order or both second order etc., a detector, a second lens for bringing said positive diffraction order and said negative diffraction order which are directed along said same path to focus on said detector, said detector producing an output of said positive diffraction order and said negative diffraction order received, and a computer for processing said output from said detector.

A system for performing selected optical measurements on a sample according to other embodiments of the invention comprises a broad band light source, a first beamsplitter for splitting light from said broad band light source into a signal beam and a reference beam, a reference mirror disposed along the path of the reference beam, the sample being disposed along the path of the signal beam, a first lens for bringing the signal beam to focus on said sample, a diffraction grating for receiving reflections from the reference mirror and producing therefrom a diffracted beam, the reflections from the reference mirror being incident on the diffraction grating such that a diffraction order from the reflections from the reference mirror is directed along a first path, a detector, a second beamsplitter for combining reflections from the sample with the diffraction order along said first path to produce a combined beam, a second lens for bringing said combined beam to focus on said detector, said detector producing an output of said combined beam received, and a computer for processing said output from said detector.

In other versions of the invention a diffraction order from the signal beam is combined with reflections from the reference beam.

A method for performing selected optical measurements on a sample according to certain embodiments of this invention comprises a method for performing selected optical measurements on a sample comprising providing a light source, splitting light form said light source into a signal beam and a reference beam, positioning a reference mirror along thee path of the reference beam, positioning the sample along the path of the signal beam, bringing the signal beam to focus on said sample, positioning a diffraction grating for receiving reflections from the sample and from the reference mirror and producing therefrom a diffracted beam, the reflections from the sample and the reference mirror being incident on the diffraction grating such that a positive diffraction order from the reflections from one of the sample and reference mirror and a negative diffraction order form the reflections from the other one of the sample and reference mirror are directed along the same path, the two diffraction orders being the same number i.e. both first order or both second order etc. providing a detector, bringing said positive diffraction order and said negative diffraction order directed along said same path to focus on said detector, said detector producing an output of said positive diffraction order and said negative diffraction order received, and processing said output from said detector.

A method for performing selected optical measurements on a sample according to other embodiments of the invention comprises providing a light source, splitting light from said light source into a signal beam and a reference beam, positioning a reference mirror along the path of the reference beam, positioning the sample along the path of the signal beam, bringing the signal beam to focus on said sample, positioning a diffraction grating for receiving reflections from the reference mirror and producing therefrom a diffracted beam, the reflections from the reference mirror being incident on the diffraction grating such that a diffraction order form the reflections from the reference mirror is directed along a first path, providing a detector, combining reflections from the sample with the diffraction order along said first path to produce a combined beam bringing said combined beam to focus on said detector, said detector producing an output of said combined beam received, and processing said output form said detector.

In some embodiments, the diffraction grating is stationary and the detector is a one-dimensional linear CCD array while in other embodiments the diffraction grating is moving and the detector is a multichannel diode array whose output is fed into a demodulator.

Various features and advantages will appear from the description to follow. In the description, reference is made to the accompanying drawings which form a part thereof, and in which is shown by way of illustration, specific embodiments for practicing the invention. These embodiments will be described in sufficient detail to enable those skilled in the art to practice the invention, and it is to be understood that other embodiments may be utilized and that structural changes may be made without departing form the scope of the invention. The following detailed description is therefore, not to be taken in a limiting sense, and the scope of the present invention is best defined by the appended claims.

BRIEF DESCRIPTION OF THE DRAWINGS:

In the drawings wherein like reference characters represent like parts.

DETAILED DESCRIPTION OF PREFERRED EMBODIMENTS

The present invention is directed to a multifunctional fast correlation-domain interferometric method and system for biomedical and nonmedical applications. The present invention involves single shot method of ultrafast correlation interferometry (UCI)I for imaging microscopic scale reflective objects. The method converts the time propagating of pulses reflected from an object into a corresponding coherence-domain interference pattern that permits the simultaneous registration of reflections by use of a stationary diffraction grating and a one dimensional CCD array in some embodiments and in other embodiments by a moving diffraction grating and a multichannel diode array and demodulator.

Figure 1:
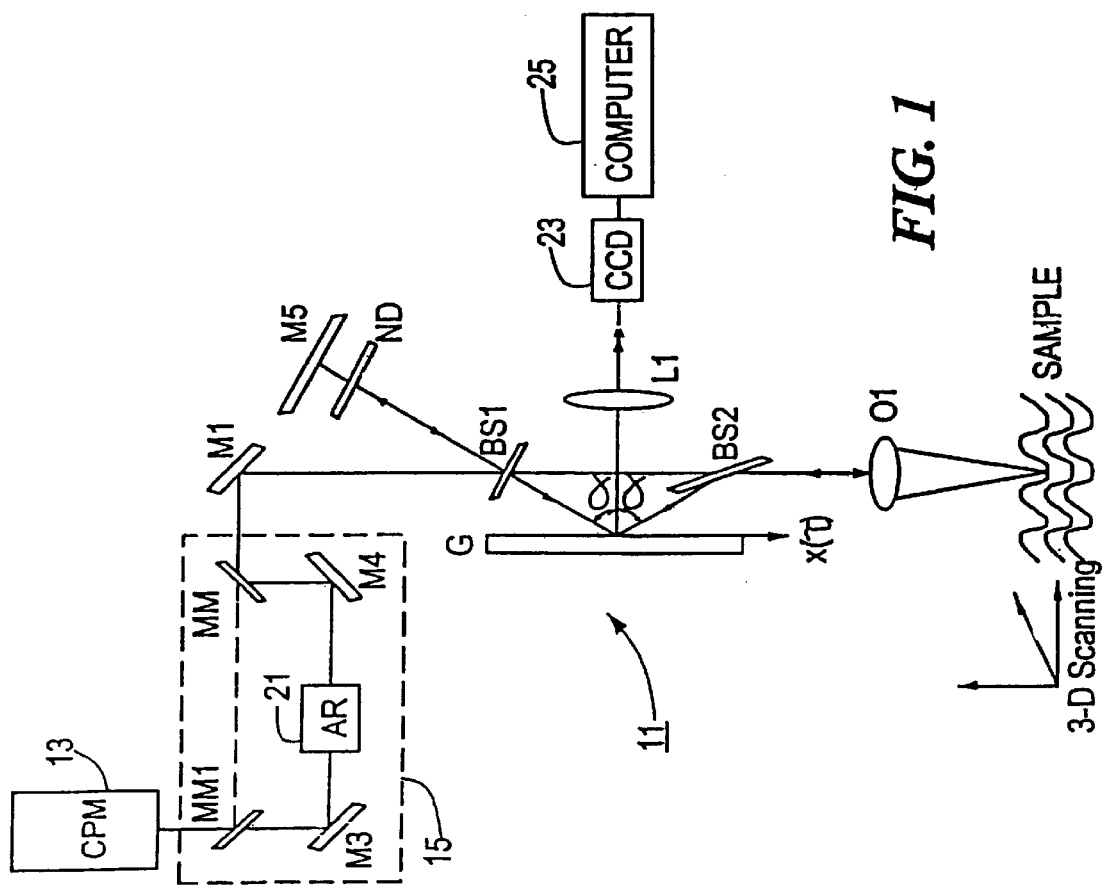
FIG. 1 is a schematic block diagram of one embodiment of a system for performing selected optical measurements of a sample constructed according to this invention.

Referring now to the drawings, there is shown in FIG. 1 an embodiment of a system constructed according to this invention and identified by reference numeral 11.

In system 11, light from a colliding-pulse mode-locked laser 13, is amplified in an amplifier apparatus 15, reflected off a first mirror M1 and strikes a first beamsplitter BS1 where it is split into a transmitted part which serves as a signal beam and reflected part which serves as a reference beam. Amplifier apparatus comprises a pair of movable mirrors MM1 and MM2, a pair of fixed mirrors M3 and M4 and an amplifier system 21.

The reference beam passes through a neutral density filter ND and strikes a reference mirror M5. Light pulses from reference mirror M5 pass back through neutral density filter ND, through first beamsplitter BS1 and are incident on a reflection diffraction grating G. Grating G is oriented so as to have vertically disposed grooves.

The signal beam transmitted through first beamsplitter BS1, passes through a second beamsplitter BS2 and is brought to focus by a spherical lens O1 on a sample S. Light pulses reflected from sample S are reflected off second beamsplitter BS2 and are incident on grating G.

The reflections from sample S and mirror M5 are incident on the grating with respect to grating normal so that a positive diffraction orders from the reflections from one of the sample S and mirror M5 and a negative diffraction order from the reflections from the other one of the sample S and Mirror M5 propagate along the normal (p sin α=λ, where p is the spacing between grooves, 1/1200 mm). The diffraction order from the reflections from sample S can either be a first order or a second order or a higher order. Similarly, the diffraction order from the reflections from mirror M5 is the same order (i.e. number) as the diffraction order of reflections from sample S.

As an example, the diffracted light from the reference beam propagating along the normal to the diffraction grating is the negative first diffraction order and the diffracted light form the signal beam propagating along the normal to the diffraction grating is the positive first diffraction order.

A lens L1 collects the diffracted light and focuses the light onto a one dimensional CCD detector 23 placed at the conjugate image plane of grating G. CCD array 23 includes an input shutter (not shown) to allow the diffraction orders from only one pulse to pass through. The output of CCD detector 23, which corresponds to a depth scan i.e. a scan in the Z direction, is fed into a computer 25 where the output from CCD 23 is processed.

Figure 2:
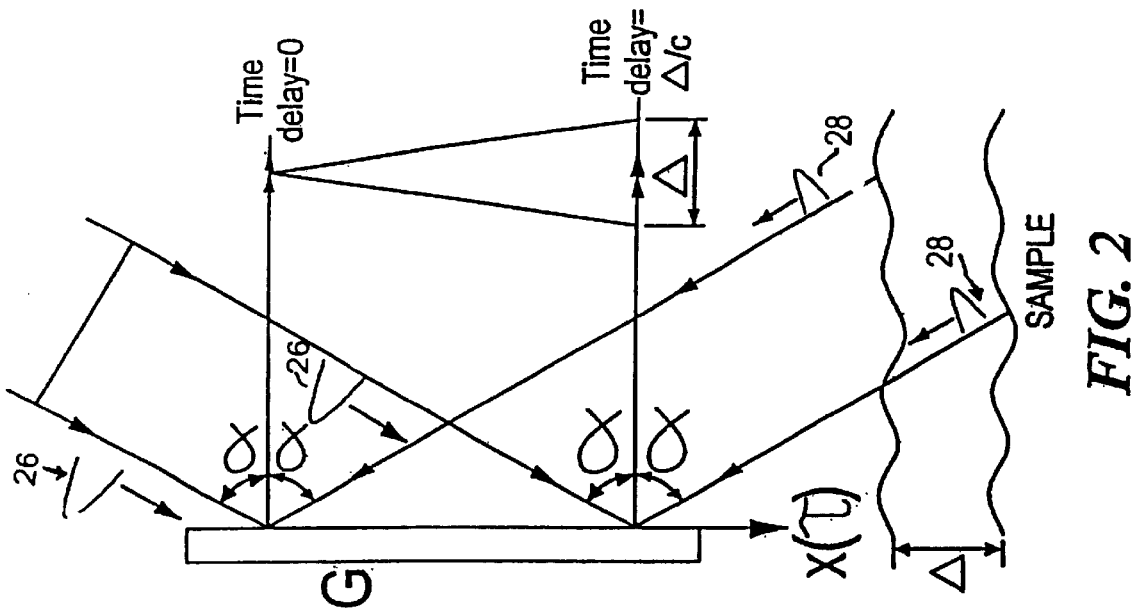
FIG. 2 is a diagram illustrating the time delay grating-generated sample depth scan in the embodiment of the invention shown in FIG. 1.

An explanation of the time delay grating-generated sample depth scan according to this invention may be better understood with reference to FIG. 2. As can be seen in FIG. 2, the diffraction grating introduces a continuous optical delay between a reference pulse 26 and a pulse 28 reflected by a sample in the direction of the grating dispersion (x axis). In this case, pulses 28 reflected by the front and back sample surfaces are split by the diffraction grating in x-direction so that interference maxima showing depth-scan reflections are also split in x-direction. The difference of optical path is $$\Delta = CT = 2x \sin \alpha = 2\lambda x/p, \quad (1)$$

where λ is the wavelength, x is the linear coordinate, and T is the time delay between the reference and signal pulses. The time-display window is given by $$T = 2\lambda D/cp \cos \alpha, \quad (2)$$

where D is the diameter of the beams. For an arrangement where D=3 mm, λ=620 nm, p=1/1200 mm, cosα=0.73 and a time-display window of $T_d$=20 ps is achieved which corresponds to a sample depth of up to 3 mm on single measurement.

Instead of a CPM laser the light source can be any broad band light source.

Figure 4:
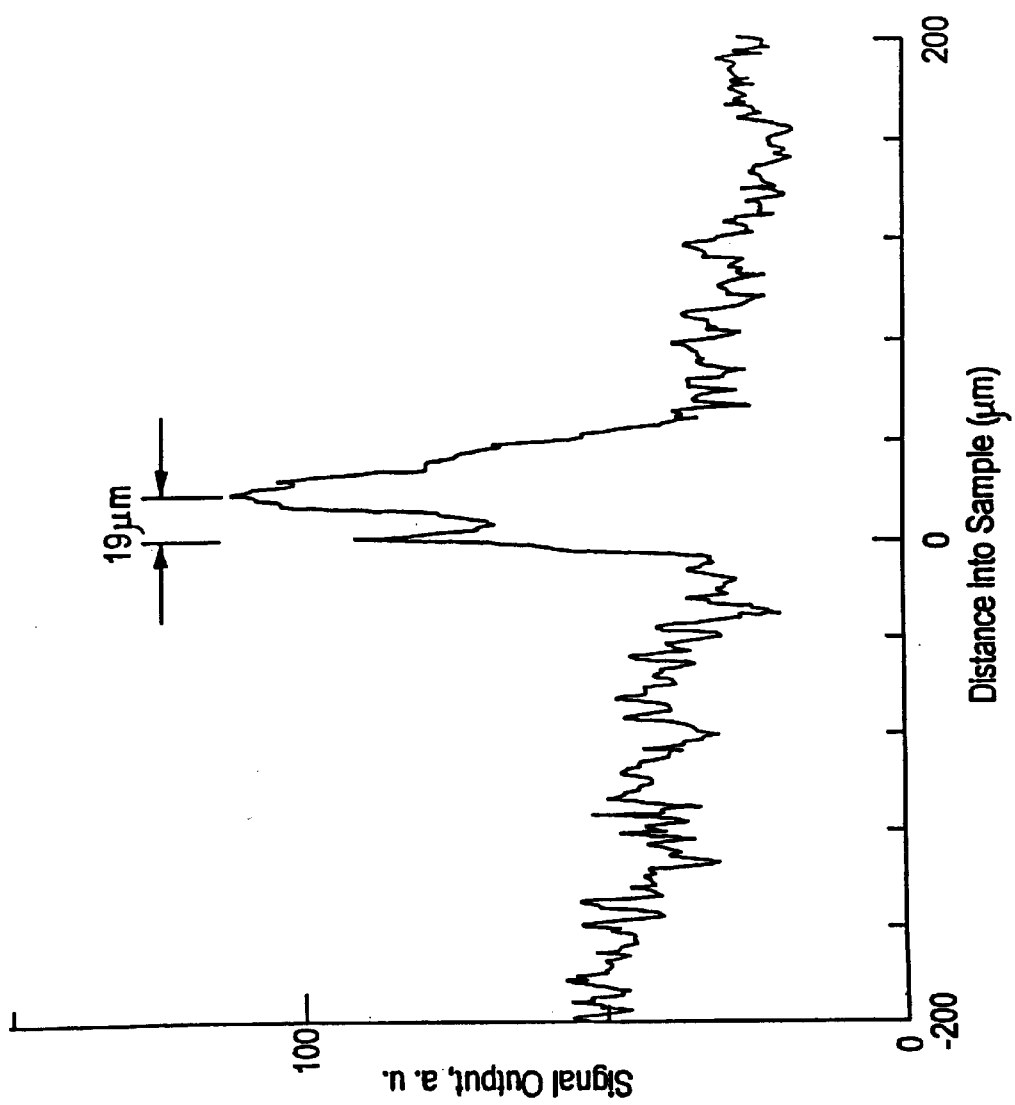
FIG. 4 is a graph of the reflectance profile across the sample shown in FIG. 3 measured using the system shown in FIG. 1.
Figure 3:
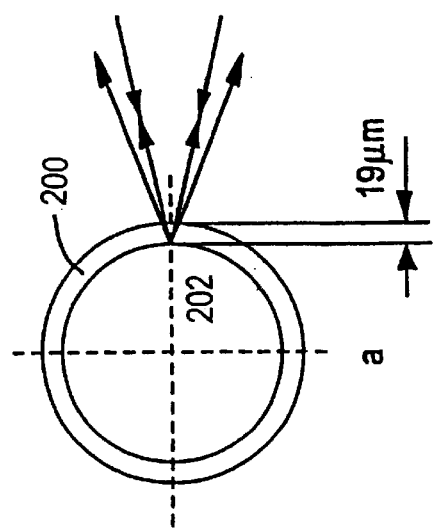
FIG. 3 is a cross-sectional view of a sample tested using the system shown in FIG. 1.

The correlation approach of this invention was tested on measuring the thickness of the cladding 200 of a single-mode fiber schematically shown in FIG. 3. The measured reflectance profile across the fiber is shown in FIG. 4. The refractive indices of the core 202 ($n_c$=1.492) and the cladding 200 ($n_{cl}$=1.417) were used to determine the reflectivity of the core-cladding boundary to be −3 3 dB and the cladding-air boundary to be −15 dB. The cladding thickness d of 19 μm (d=Δ/2$n_{cl}$ is distance into sample, Δ is optical delay) was determined.

This system is also described in an article by I. Zeylikovich and R. R. Alfano in Optics Letters Vol. 21, No. 20 Oct. 15, 1996 pp. 1682–1684, which article is incorporated herein by reference.

The ultrafast method of this invention has potential applications for noncontact diagnostics of reflective biological and medical structures to yield the histological picture of tissue because of it insensitivity to mechanical instability. Each reflective layer at depth $z_i$ will be obtain as a signal to map its location.

As will hereinafter be shown, an interferometric system according to this invention can be used for optical communications as a receiver of a pulse code signal, retrieved from an optical memory system, for example, hole-burning holography. An accumulated photon echo read-out speed as fast as 27 Terabit per second was demonstrated using this single shot crosscorrelation method for a femtosecond four-pulse packet stored by spectral hole burning in a octaethylporphine-doped polystyrene sample.

Figure 4A:
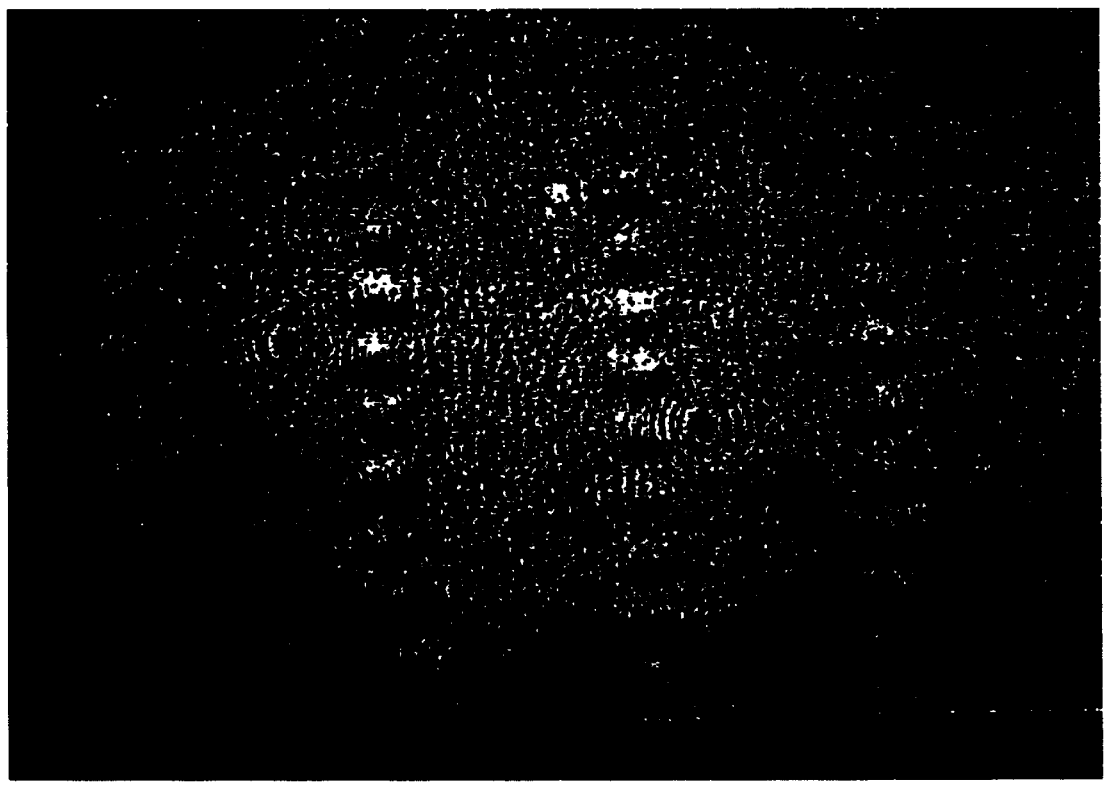
FIG. 4(a) is a CCD image of a single shot interference pattern.
Figure 5:
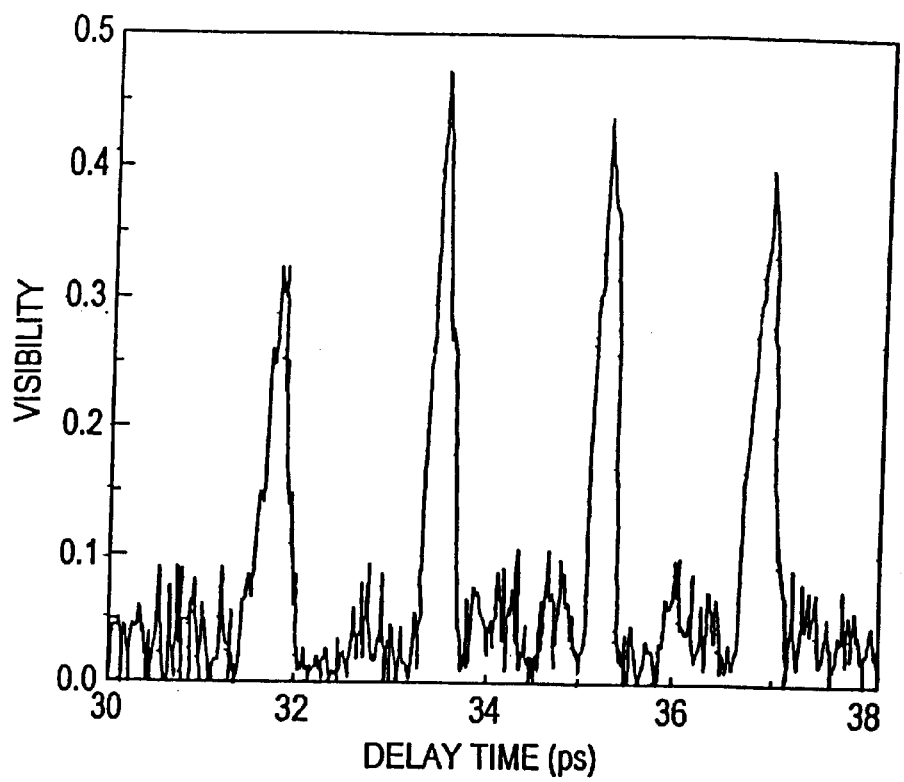
FIG. 5 is a digitized cross correlation trace obtained using the system shown in FIG. 1.

FIG. 4a demonstrates the crosscorrelation detection of an echo four-pulse packet on a single-shot basis. A CCD image of the single-shot interference pattern (between the recalled echo four-pulse packet and a cross-reference pulse) is displayed in FIG. 4a and the corresponding digitized crosscorrelation trace is shown in FIG. 5. The echo pulses are separated by 1.7 psec. The interference pattern and cross-correlation of the echo signals demonstrates the good single-shot reproduction of the temporal profile of the initial pulse packet and provides 4 bits of information per 150 fsec which corresponds to a data read-out speed of 27 Terabit/sec.

This invention can be used to produce an interference 2D (depth-transversal coordinate) image of biological tissue with acquisition time as short as 20 ms. This method of grating-generated interference microscopy called GIM is applied to produce a high resolution image of skin tissue.

Figure 6:
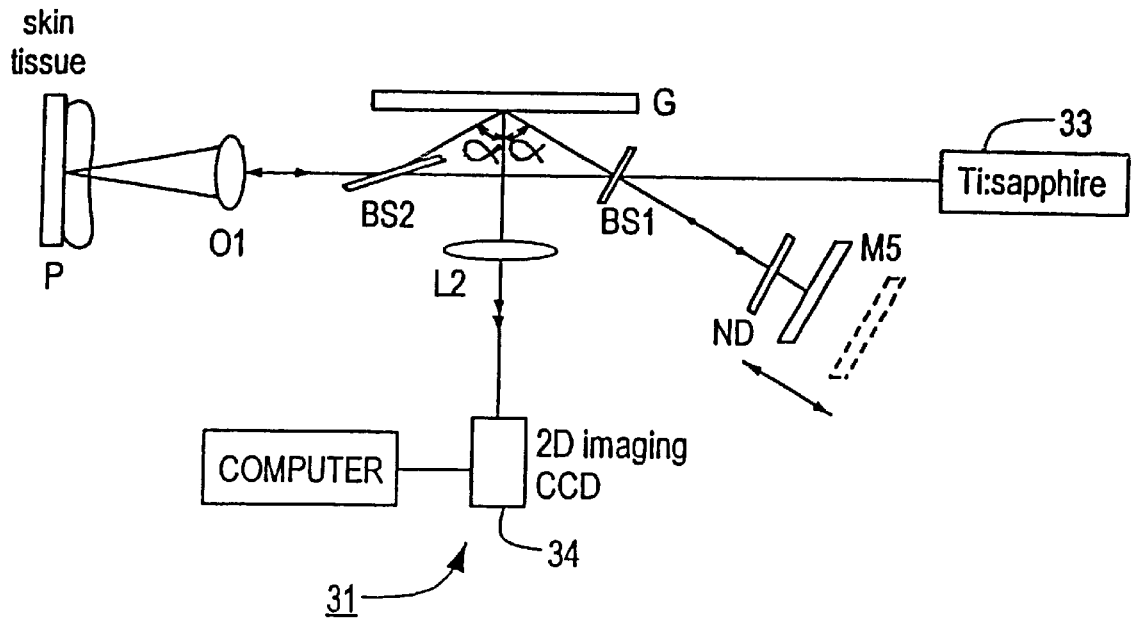
FIG. 6 is a schematic block diagram of another embodiment of a system for performing selected optic al measurements of a sample constructed according to this invention.

A schematic diagram of an experimental system used to illustrate the invention for obtaining a 2D image is shown in FIG. 6 and identified by reference numeral 31. System 31 differs from system 11 in that amplifier apparatus 15 is omitted, the light source is a Ti:Sapphire laser 33 rather than a CPM laser, L2 is a cylindrical lens, O2 is an objective lens and CCD 34 is a 2D imaging array. The chicken skin tissue sample (about 3 mm of thickness) is attached to the glass plate (P) surface. The signal beam is focused by the lens O (f=5 cm) onto the surface of glass plate P so that the beam spot size on the chicken skin surface is about 0.3 mm which determines the transversal coordinate image. The grating plane is optically conjugated with a 1024×1024 pixel CCD array by the lens L2 which records the 2D interference image.

The diffraction grating introduces a continuous optical delay (producing biological depth scan) in the direction of the grating dispersion (x axis). For the experimental arrangement described above, D=2.5 mm, $\lambda$=800 nm, p=$\frac{1}{600}$ mm, $\cos\alpha$=0.877 and a time-display window of $T_d$=13.5 ps is achieved which corresponds to a sample depth scan of up to 2 mm.

After CCD registration of the first interference pattern defined as a signal, a second CCD exposure defined as a reference is applied for which interference between reference and signal pulses is destroyed.

The dynamic range (DR) of GIM is defined by the ratio of the largest measurable CCD interference signal to the noise (SNR):

$$DR=10 \log(SNR=1). \quad (3)$$

There are several noise sources such as the readout CCD system noise (in the dark), optical measurements noise:

$$SNR=W^2_{max}/W^2_{min}=(\rho_{sj})^2_{max}/(\rho_{sj})^2_{min}, \quad (4)$$

where W is the CCD camera detected signal, which is proportional to the light impinging at the CCD array and $P_s$ is the sample amplitude reflectivity. The dynamic range of GIM depends on the DR of the CCD array. The SNR of the CCD camera is equal to the ratio ($W_{max}/W_{min}$), then $(DR)_{max}=(DR)^2_{ccd}$. The CCD camera with "14 bit DR" has a DR of approximately $1.6\times10^4/1$, which leads to a potential dynamic range $(DR)_{max}$ of 80 dB.

The sensitivity (S) of GIM is defined as:

$$S=10 \log[(\rho_{sj})^2_{min}]. \quad (5)$$

Using Eqs. (3 to 5), the sensitivity of GIM is expressed as:

$$S=10 \log[(\rho_{sj})^2_{max}]-DR. \quad (6)$$

The maximum CCD output signal occurs when the amplitudes of reference and signal pulses are equal. Take into account that $W^2_{max}$ can be changed, introducing a neutral density filter in the reference beam then filter double-pass optical density $(OD)_{ref}$ is equal $$(OD)_{ref}=-\log[(\rho_{sj})^2_{max}]. \quad (7)$$

Using Eq.(6 and 7) the sensitivity can be expressed by:

$$S=-10(OD)_{ref}-DR. \quad (8)$$

Equation (8) shows an important feature of GIM. S can be increased independently of the GIM DR. For our setup $(\rho_{sj})^2_{min}=10^{-10}$, DR=70 dB, and Eq. (8), $(OD)_{ref}$ is calculated to be 3.

Figure 7:
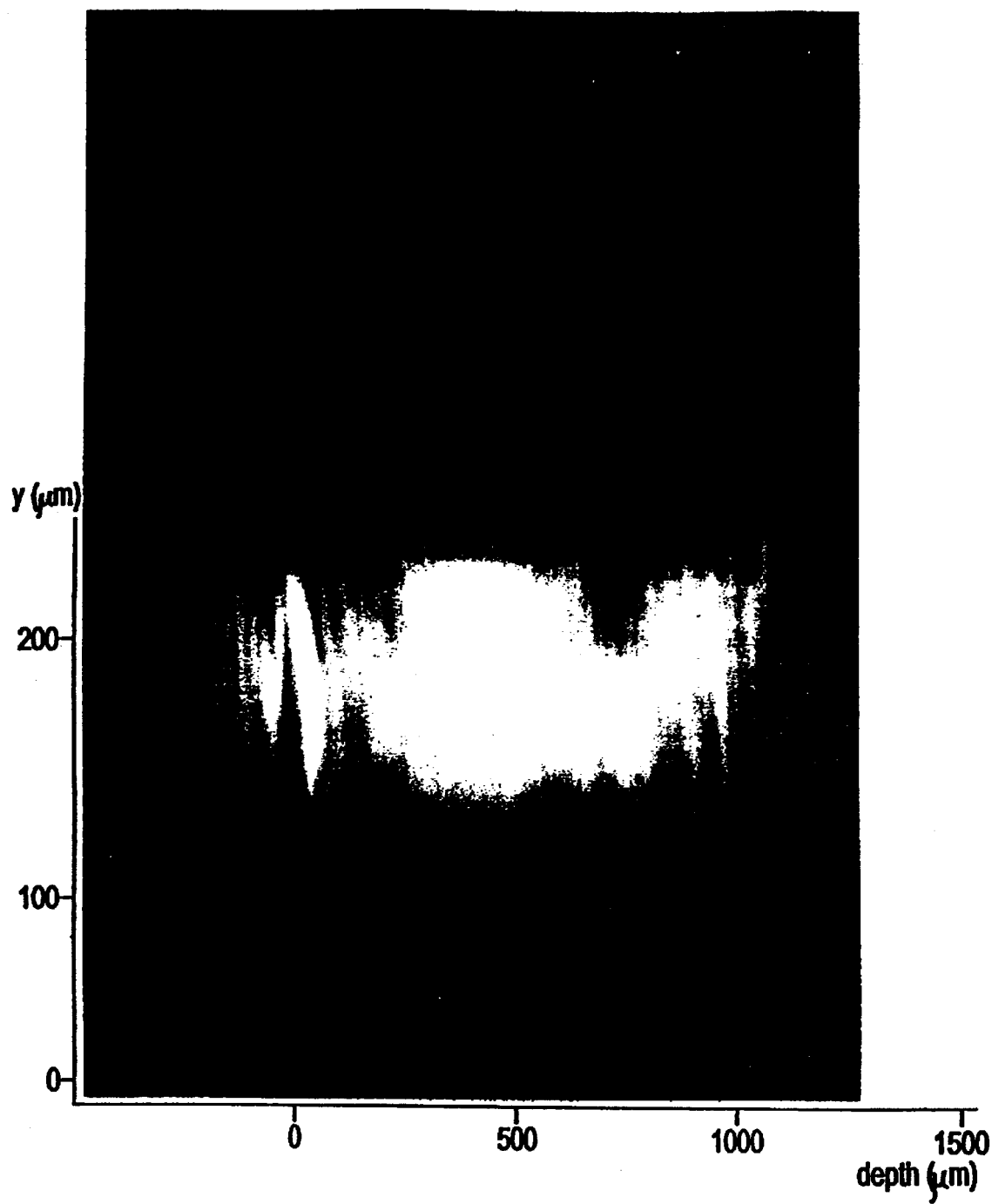
FIG. 7 is a 2D interference image obtained using the system shown in FIG. 6.

A 2D interference image (after subtraction of a signal and a reference images) of the chicken skin tissue is shown in FIG. 7. FIG. 7 illustrates a two-dimensional depth-transversal coordinate chicken tissue image.

A rapid 20 ms acquisition time to acquire 2D image for laser power (TI:sapphire) of 30 mw is achieved. This time is ten times faster than other methods. The transversal high resolution structures of the skin, a membrane and muscle are visualized for the depth of up to 1.5 mm. The time-display window is given by $\gamma_d=2\lambda D/cp \cos\alpha$, where D is the diameter of the beams. In the setup performed, D was 2.5 mm, $\lambda$=800 nm, p=$\frac{1}{600}$ nm, $\cos\alpha$=0.877 and a time-display window of $\gamma_d$=13.5 ps was achieved which corresponds to a sample depth scan of up to 2 mm.

Figure 8:
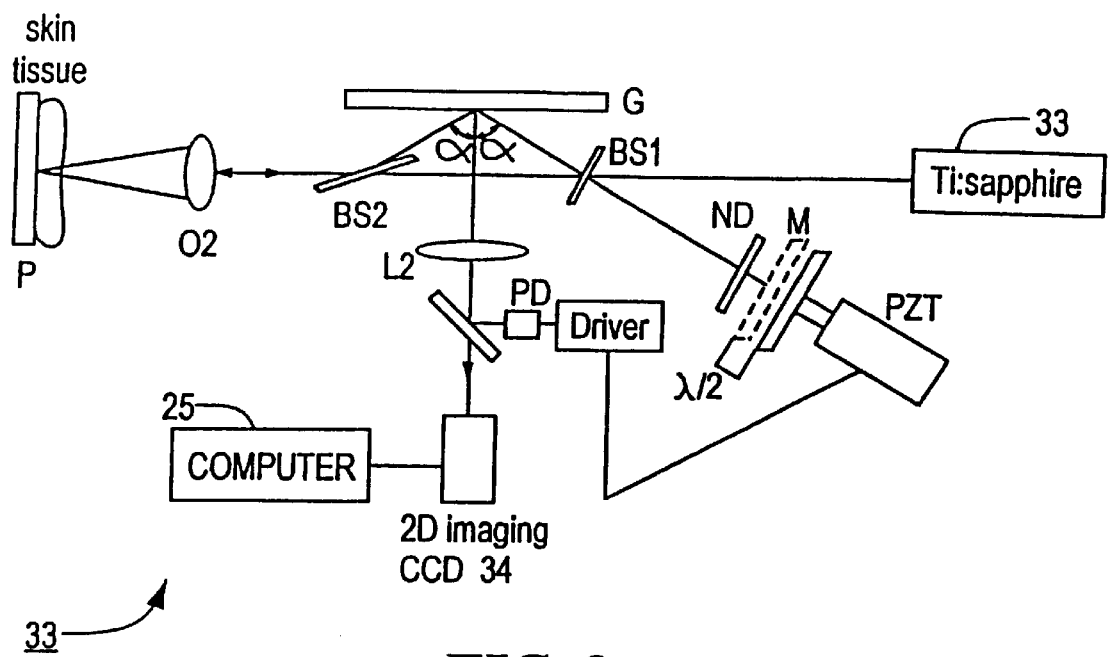
FIG. 8 is a schematic block diagram of a modification of the system shown in FIG. 6.

Another way to increase the system sensitivity and dynamic range of the interferometric system is shown in system 33 in FIG. 8. In system 33, reference mirror M5 is moved by a PZT transducer 35 into two positions with the path difference equal to $\lambda/2$, where $\lambda$ is the source central wavelength. The positions of reference mirror M5 is managed by a photodetector-PZT feedback loop 37 to acquire two images, one background+signal and the other background−signal, corresponding for the two positions of the PZT. Feedback loop 37 comprises a driver 39 and a photodetector 41. These two images are subtracted to produce 2D (depth-transversal coordinate) dark-field interference image with double sensitivity. In this way the background is removed and the signal is doubled (Background+signal)−(background−signal)=Two times the signal.

Figure 9:
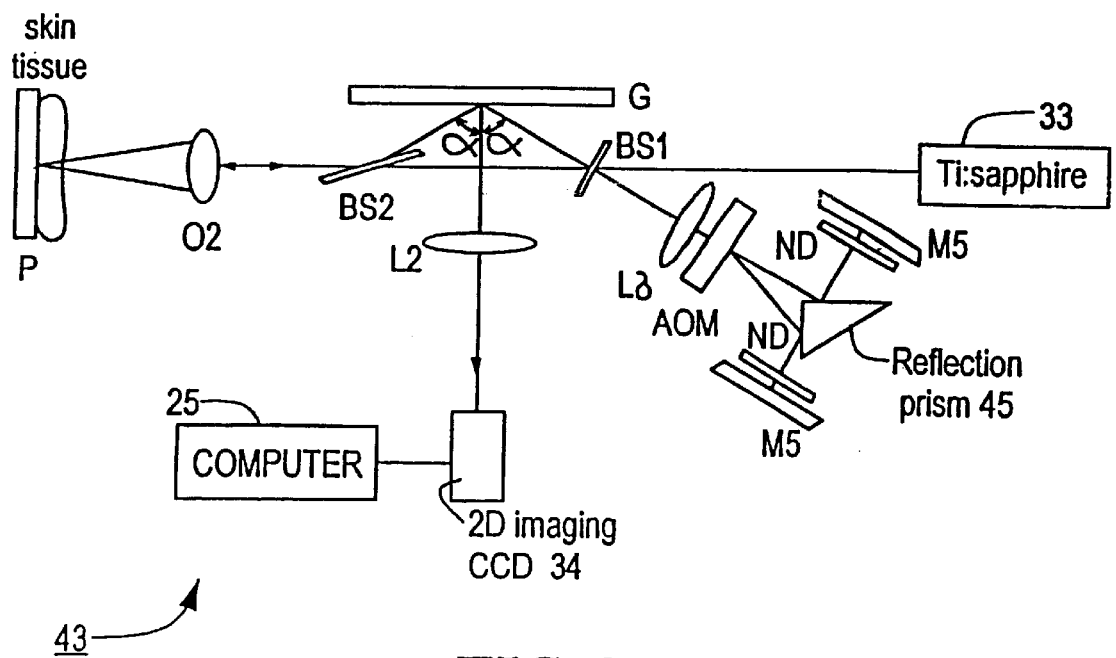
FIG. 9 is a schematic block diagram of another modification of the system shown in FIG. 6.

In order to increase the data acquisition speed and remove background the interferometric system can be constructed as shown in FIG. 9. In the system in FIG. 9, which is identified by reference numeral 43, there is a focusing lens L3, acousto-optical modulator (AOM), a 90° reflection prism 45, two neutral density filters ND and two reflection mirrors M5. Mirrors M5 are located so that the beam deflected by modulator AOM and reflected by the sides of prism 45 and one of the mirrors M5 is directed back to the diffraction grating G at the diffraction angle −$\alpha$. The CCD frames with and without interference are subtracted sequentially one from another to produce a series of the 2D (depth-transversal coordinate) dark-field interference images. The remainder of system 43 is substantially identical to system 31 in FIG. 6.

For the grating-generated coherent scans with single-shot pulses the time response of the CCD linear array-computer memory is 1 ms. The repetition rates cannot be better than $10^3$ I.p./s. (Lateral pixels per second). As can be appreciated, a reference pattern is needed for each axial scan to reduce the background. Full axial scan needs at least 2 ms with repetition rates of 500 I.p/s. Using the repetition rates of 500 I.p/s and the artery scan time of 20 ms only 10 lateral pixels will be produced. This system can be useful for imaging of objects with very fast deviations in axial direction but with the small size of sample in the lateral direction. Therefore, additional methods are needed to increase data acquisition speed, sample scanning size and signal to noise ratio of the optical correlation-domain imaging.

Figure 10:
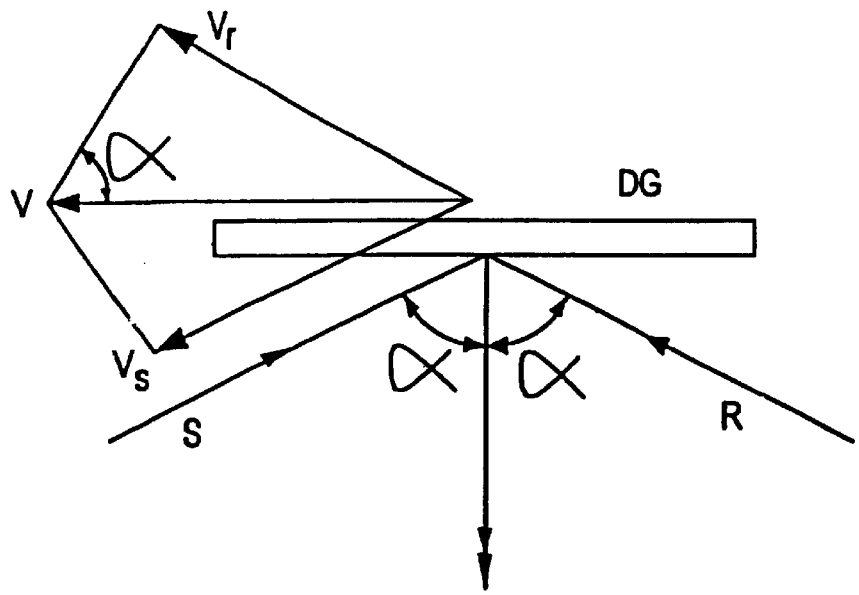
FIG. 10 is a schematic diagram useful in understanding another embodiment of the invention.

Another version of this invention utilizes the principal that when a light beam is diffracted by a moving diffraction grating (DG), the frequency of the diffracted light has a Doppler shift. Consider a diffraction grating DG moving in the direction of the grating dispersion (x-axes) with constant speed v, as can be seen in FIG. 10, the projections of the speed vector V on the direction of the reference (signal) beam are $V_{r,s}=\pm v \sin\alpha$, where $\pm\alpha$ is the angle between the reference (signal) beams and the normal to grating DG. The Doppler frequency shift (DFS) between diffracted reference and signal beams is $$\Delta f_D = 2vf_o \sin\alpha/c = 2v \sin\alpha/\lambda o = 2v/p, \qquad (9)$$

where p is the space between DG grooves and fo, and λo are light frequency and wavelength, respectively.

Eq. (9) shows that DFS does not depend upon the wavelength of the broadband source. This allows using a very narrow bandpass filter in a demodulator to increase SNR. This approach differs form other approaches wherein $\Delta f_D$ depends on λ. For example, if v=30 mm/s and p=0.001 mm, then $\Delta f_D$=230/0.001=60 Khz. The output interference signal will be temporally modulated with a frequency equal of $\Delta f_D$.

Figure 11:
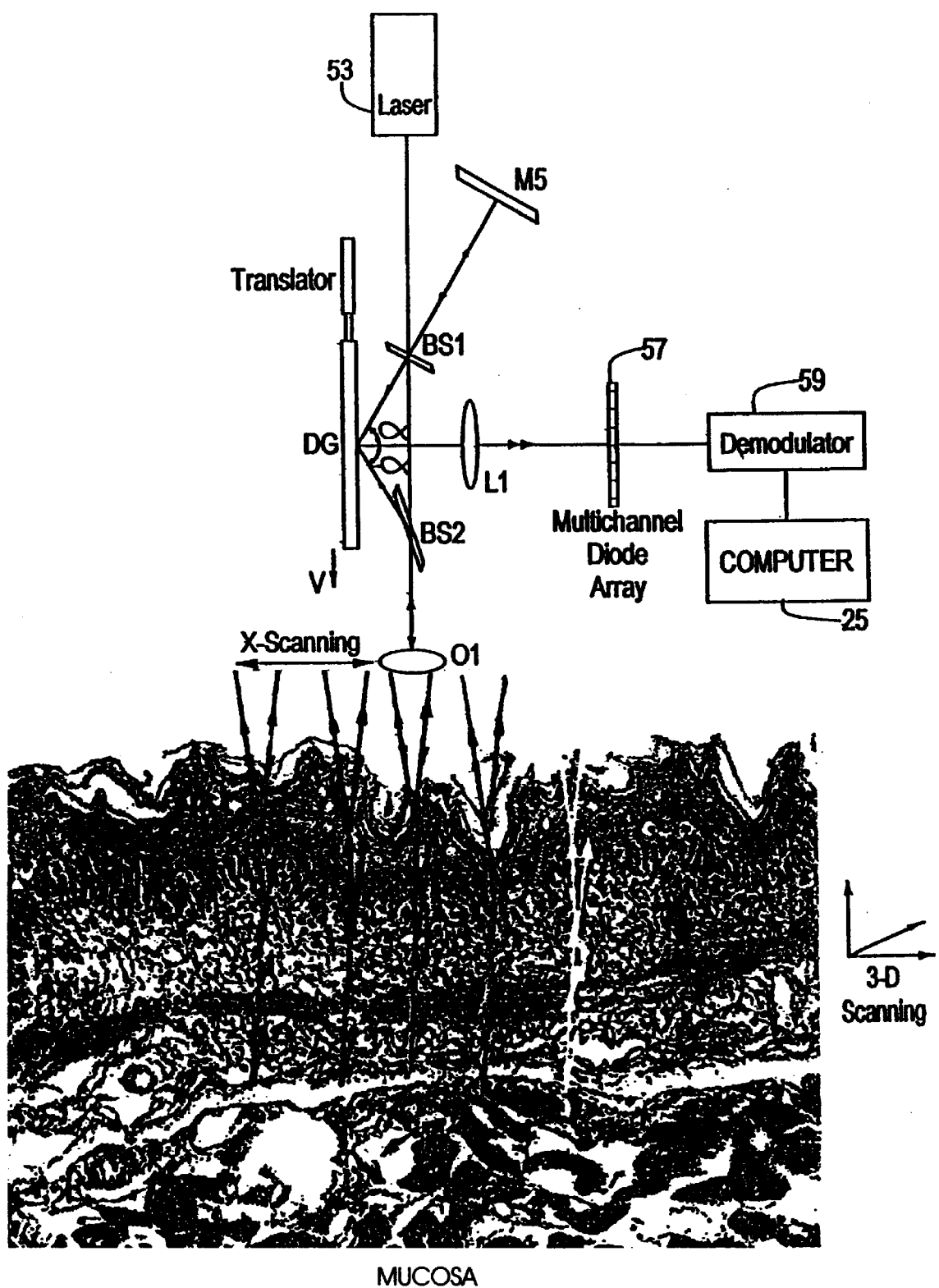
FIG. 11 is a schematic block diagram of another embodiment of a system for performing selected optical measurements of a sample constructed according to this invention.

A system illustrating a moving grating arrangement and identified by reference numeral 51 is shown in FIG. 11. System 51 includes a laser light source 53, a first beamsplitter BS1, a second beamsplitter BS2, a grating DG, a reference mirror M5 a translation 55 for moving grating DG, a focusing lens 01, a collection lens L1, a multichannel diode array 57, a demodulator 59 and a computer 61. System 51 differs from system 31 mainly in that the grating is movable and that the detector is a multichannel diode array and a demodulator. As can be seen, the optical signal from grating DG (i.e. the diffracted light) is directed to multichannel linear array (L.A.) detector 57. The optical signal is detected by demodulating the multichannel diode array detector 57 output at the Doppler shift frequency (DSF). The output signal $W_j(T)$ is given by:

$$W_j(T) \sim \rho_{sj} |Y(T-T_j)|, \qquad (10)$$

where $\rho_{sj}$ is amplitude reflectivity (square-root of the intensity reflectivity) of j-th boundary inside the sample, $|Y(T-T_j)|$ is the degree of coherence. The summation in Eq. 4 shows that each signal reflection produces a contribution to interference pattern proportional to the reflectivity $\rho_{sj}$. The signal coming from the reflecting layers spread inside the object with different time delays produces a contribution to the interference pattern proportional to the layer reflectivity $\rho_{sj}$. The full width at half maximum (FWHM) of each reflectivity peak will be equal to the amplitude correlation time, (FWHM of the degree of coherence $|Y(T-T_j)|$ determining the resolution of this method. The accuracy with which reflection-site location can be determined depends only on the resolution of the diode array. If $\Delta f_D$=60 Khz than the processing time of the each diode array pitch AC signal is about $10/60 \times 10^3 \approx 0.1$ ms. The processing of the AC signals are performed in parallel for all pitches. The time response of 0.1 ms for each axial scan and the scan repetition rates of $10^4$ l.p./s can be reached. For frequency-modulated interferometry the signal to noise ratio (SNR) of 100 dB may be achieved. This method performs high-resolution cross-sectional imaging by illuminating tissue with low-coherence light and measuring the back scattered light as a function of grating-generated time delay or range at different transverse positions.

In the system shown in FIG. 11, the sample S is mounted on a stage (not shown) which is movable by means (not shown) in the "X" and "Y" directions so as to provide 3D imaging.

The system in FIG. 11 provides a noncontact, high-sensitivity, high-resolution technique for optical imaging. High scan speeds are especially relevant for medical and biological diagnostic applications. Histological architecture of eye and tissue is of special interest is the noninvasive measurement of anterior eye dimensions and tissue diagnosis. In addition to diagnostics in biological systems, high-speed grating-generated depth scan has numerous applications for noncontact diagnostics of precision mechanical and optical systems as well as for process control and monitoring in manufacturing.

This technique for performing an optical histological map (high-resolution micrometer-scale cross-sectional optical imaging) of tissue architectural morphology, such as an artery internal structure or internal structure of a mucous without the need to excise tissue specimens, would have a powerful effect on the diagnosis and clinical management of changes in tissue.

Intravascular ultrasound is an existing catheter-based technique for obtaining cross-sectional images of human vasculature. However, the technique of this invention has the capability to image vascular lesions with much higher resolution and may be clinically useful for performing high-resolution imaging of other organ system, such as the artery, skin or GYN, GI tract or bladder.

Figure 12:
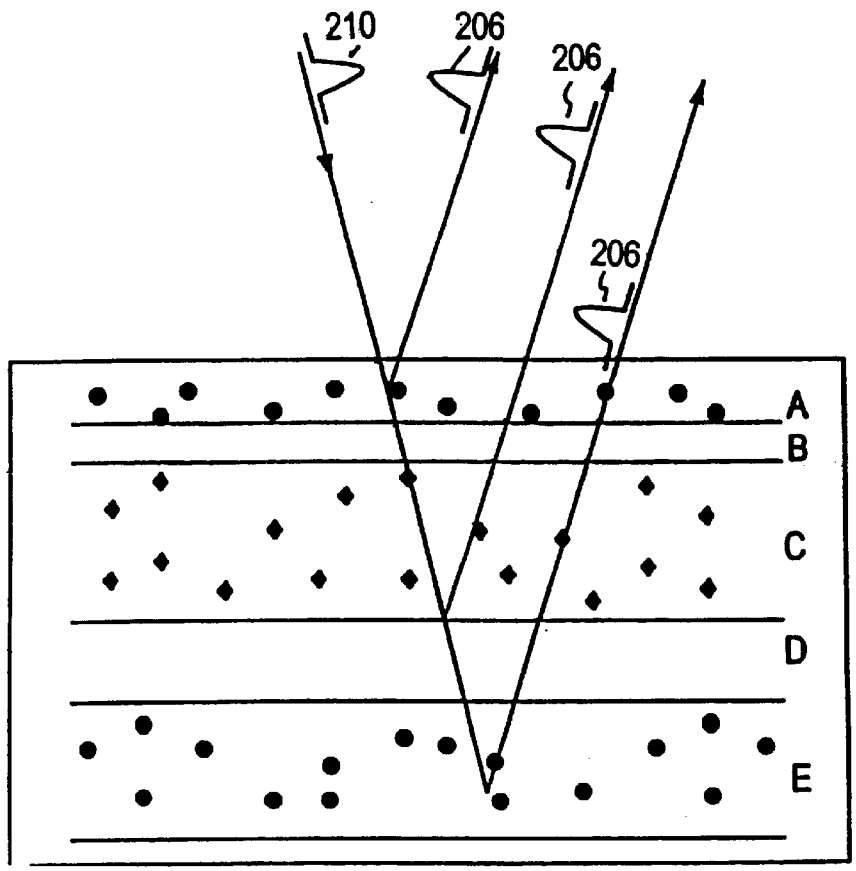
FIG. 12 is a cross-sectional structure of an oil painting and an incident pulse impinging thereon.

Cross-sectional analysis of paint samples by conventional or confocal incident light microscopy is routinely implemented during the initial examination of paintings undergoing conservation to study the structure of materials used and to identify their components. The technique of this invention has a number of important benefits over usual microscopy not least the increase in image resolution that can be obtained and the ability to produce high-speed serial optical sections of narrow Z-depth with high signal to noise ratio of 100 dB which can then be rendered into 3-d image. A major advantage of the technique of this invention is that it provides a quick and comparatively inexpensive method for accurately determine the boundaries of layers in a painting and their thickness. This technique can be used to determine if any overpainting has taken place, possibly due to previous conservation and, at high magnifications, sensitivity, could be used to identify pigment particles. A diagram to illustrate the typical cross-sectional structure of an oil painting is shown in FIG. 12, where (A) is particulate dirt deposits; (B) is varnish layer; (C) paint layer (pigment particles in a drying oil medium); (D) ground layer (lead white in a drying oil medium); Canvas support (usually linen) impregnated with size (usually animal glue). The incident pulse 210 is reflected by these layers. The time delay between reflected pulses 206 and pulse intensity consist information about the layers depth and reflectivity. This information can be extracted using the interferometric system of this invention.

Combining the properties of the grating-generated coherent depth scan, Doppler frequency modulated interference and the multichannel detector parallel registration the increasing of the data acquisition speed and spatial resolution are achieved.

Figure 13:
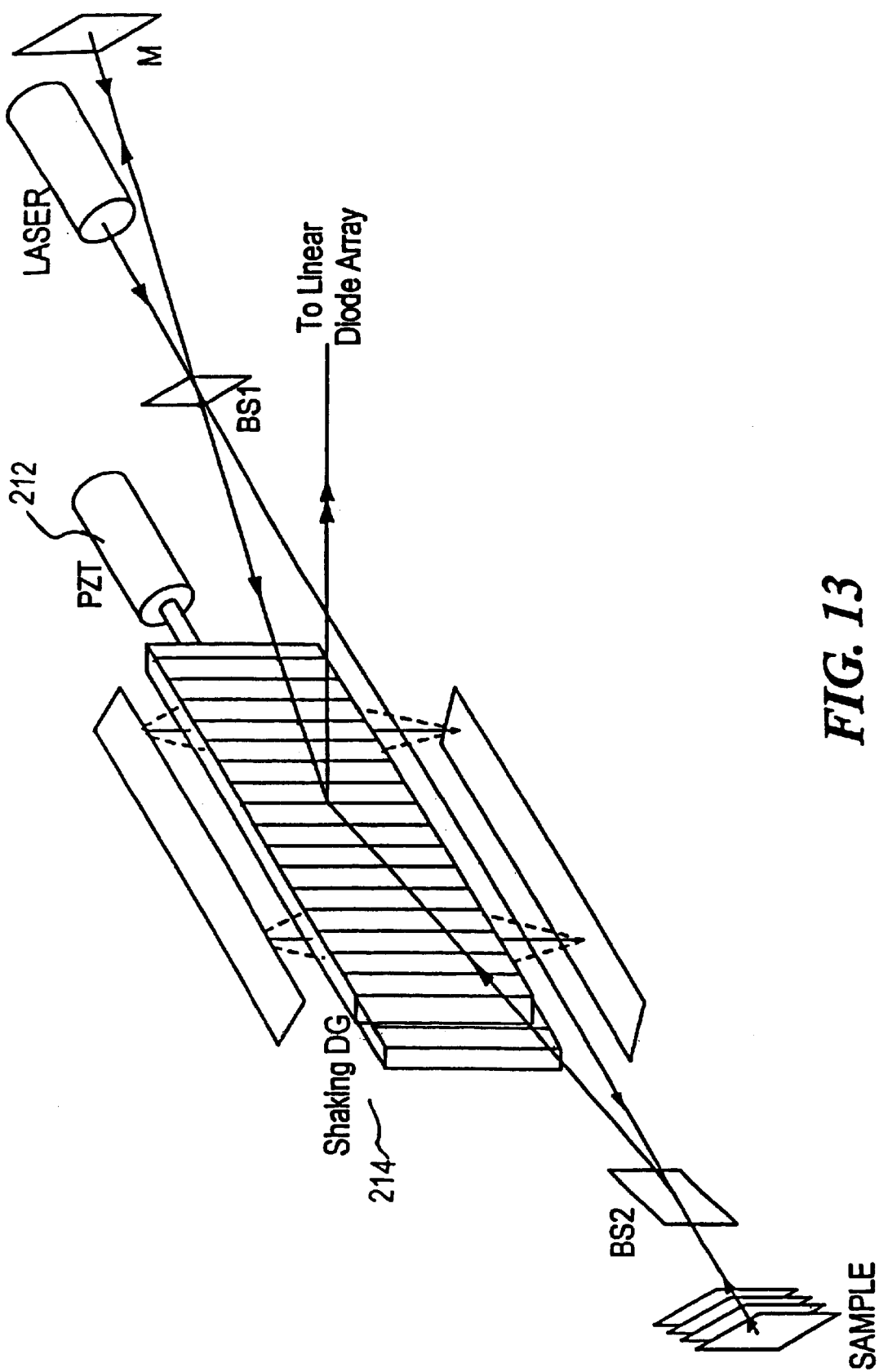
FIG. 13 is a schematic block diagram of a modification of a portion of the system shown in FIG. 11.

The DFS between diffracted reference and signal beams can be also obtained if the DG 214 is shaken along its plane as shown by arrow B by a piezotransducer (PZT) 212 so that grating displacement is more than the grating groove space (See FIG. 13). This technique can simplify the interferometer mechanical part.

Figure 14:
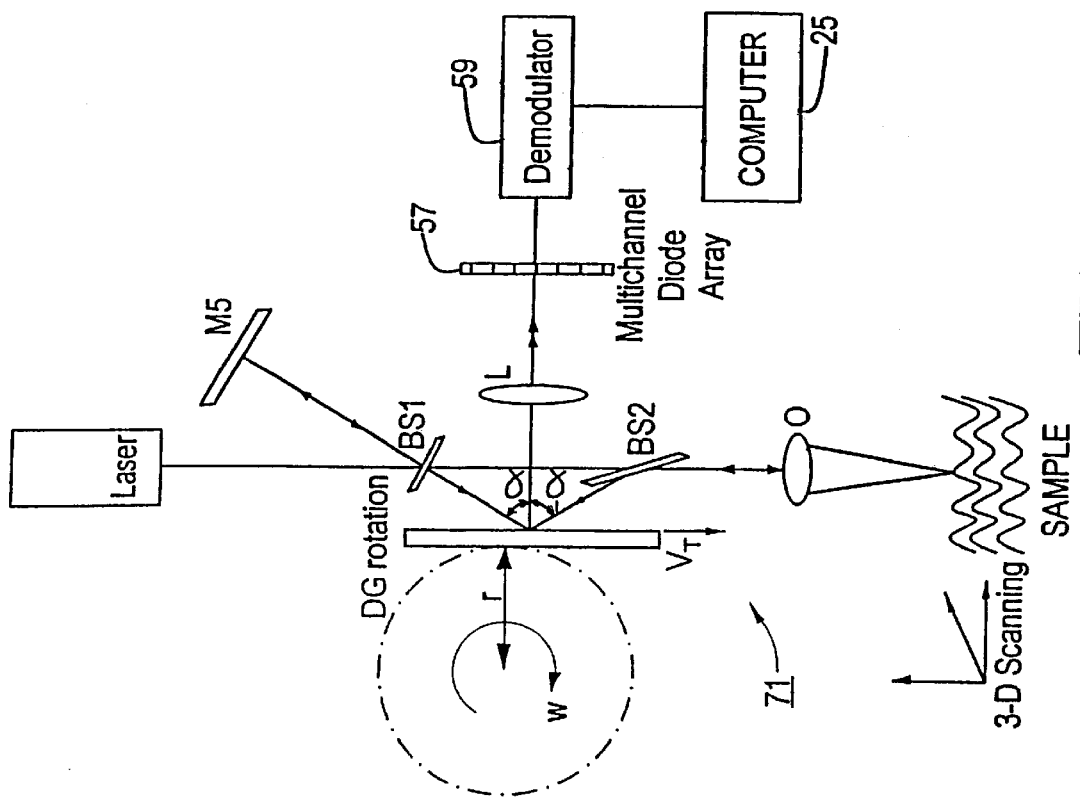
FIG. 14 is a schematic block diagram of another modification of the system shown in FIG. 11.

According to another aspect of the invention the acquisition speed is increased by using a diffraction grating that is rotating at a constant angle speed ω. Increasing of the grating tangential speed Vt is achieved in system 71 shown in FIG. 14. In system 71, grating DG is attached by an arm 73 (not shown) to the drive shaft 75 of a motor (not shown). If $\omega=8 \cdot 10^3$ rpm and radius of the circle is of 5 cm than $Vt=\omega r=2\lambda 8\times 10^3 \times 50/60=4\times 10^4$ mm/s and DFS $\Delta f_D=2\omega r/p=2\times 4\times 104/10^{-3}=80$ MHz. The AC signal processing time of the each diode array pitch is about $10/8\times 10^7 \approx 0.1$ $\mu$s. The time response of 0.1 $\mu$s for each axial scan and scan repetition rates (SRR) of 100 I.p./s can be realized.

There are several ways to increase the data acquisition speed.

Figure 15:
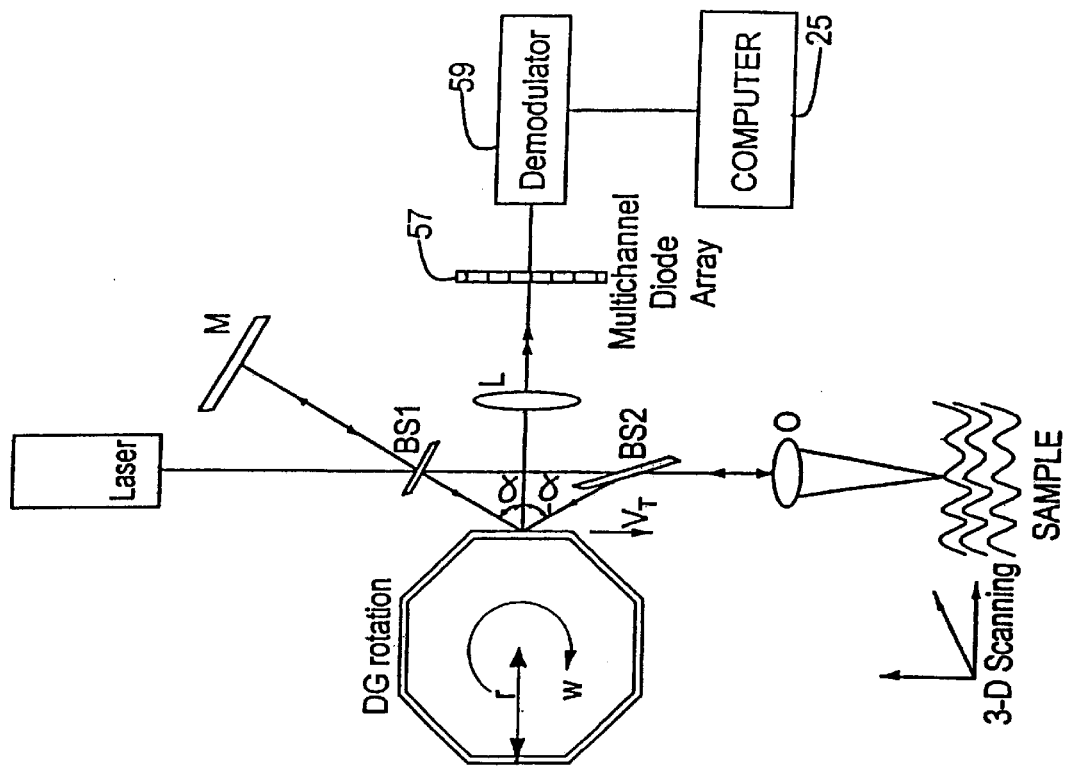
FIG. 15 is a schematic block diagram of another modification of the system shown in FIG. 11.
Figure 16:
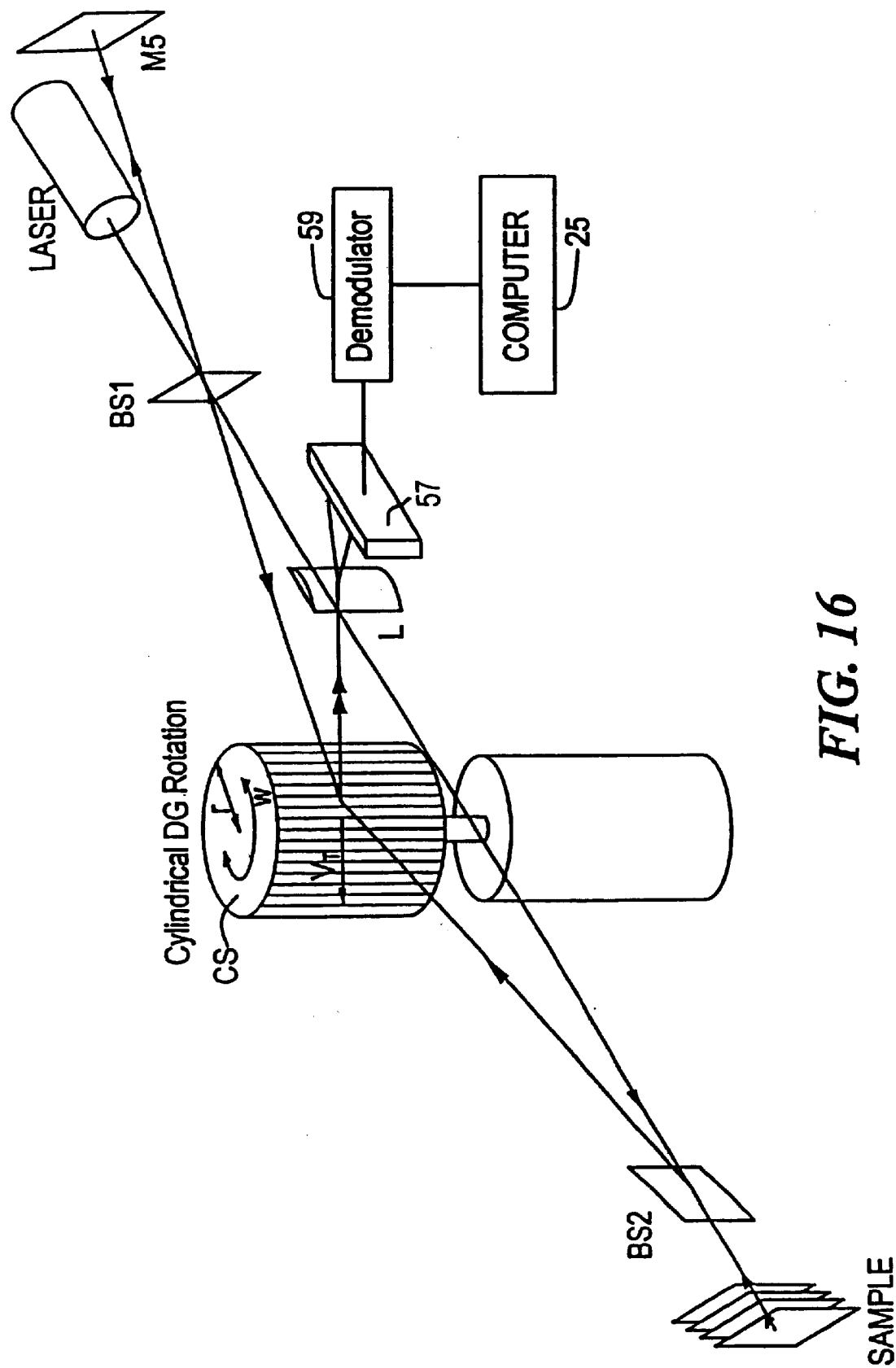
FIG. 16 is a schematic block diagram of another modification of the system shown in FIG. 11.
Figure 17:
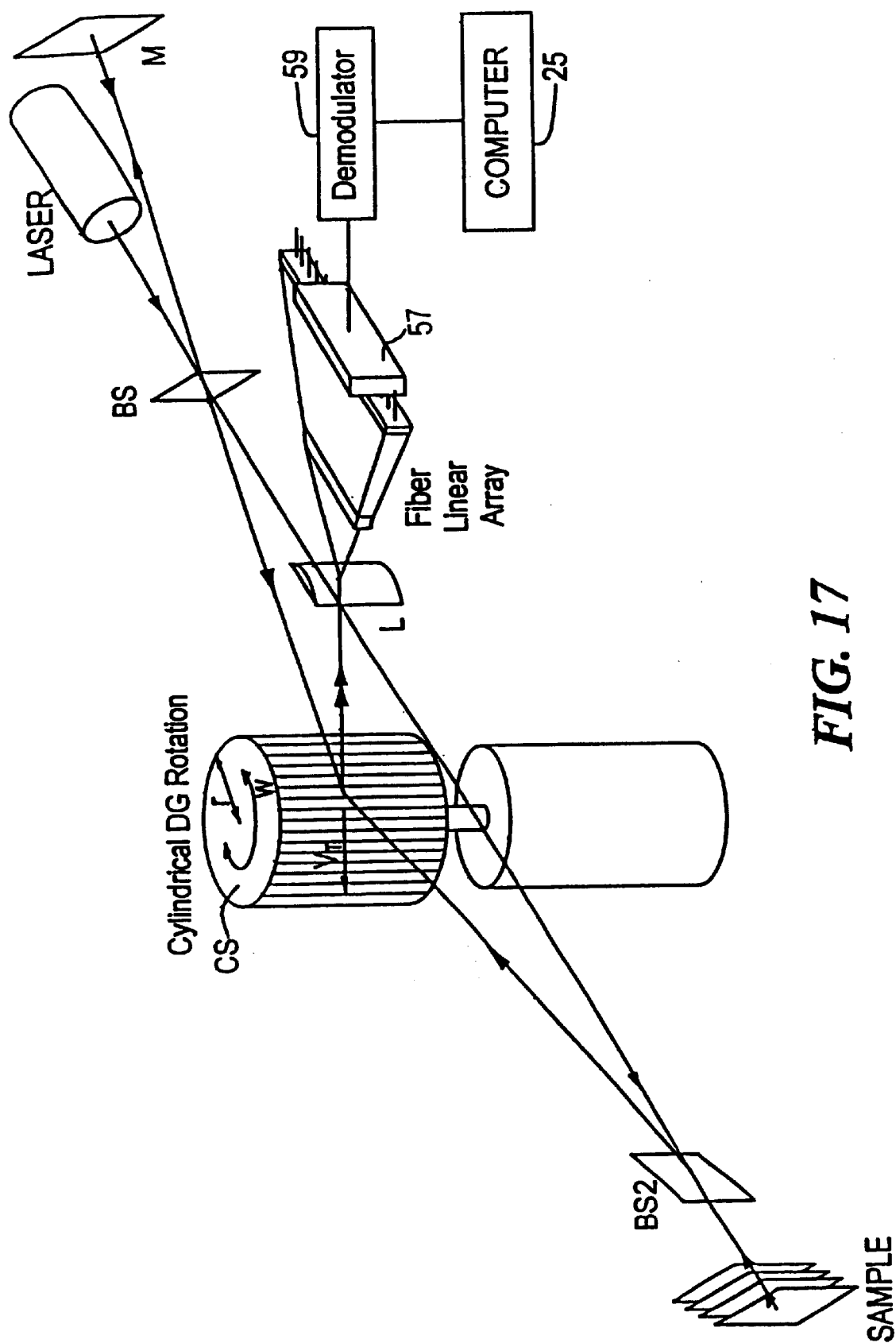
FIG. 17 is a schematic block diagram of a modification of the system shown in FIG. 16.

One way to increase the data acquisition speed is to increase the SRR use several diffraction gratings disposed on the sides of a multisided cylindrical device (See FIG. 15). These grating are rotated around the longitudinal axis of the device and the signal beam is discretely scanning in the x (or y) direction so that position of each rotating grating is synchronized with a certain x (or y) position of the scanning system. About 30 gratings of the 1 cm length can be used for the circle radius of 5 cm. The SRR is $3\times 10^3$ I.p./s. 2). If the diffraction grating is carried on cylindrical surface CS rotating with constant angle speed the maximum of the SRR and the lateral resolution can be realized (See FIG. 16). The SRR is 1 Mhz for 0.1 $\mu$s axial scan time response. To increase the axial resolution, the interference image output is collected by the fiber linear array FLA (See FIG. 17). Each fiber output is connected with a certain diode array pitch. The size of the each L.A. diode pitch is of 1 mm. The diameter of the single-mode fiber is about 100 $\mu$m and the tenfold increasing of the axial resolution can be achieved.

Figure 18:
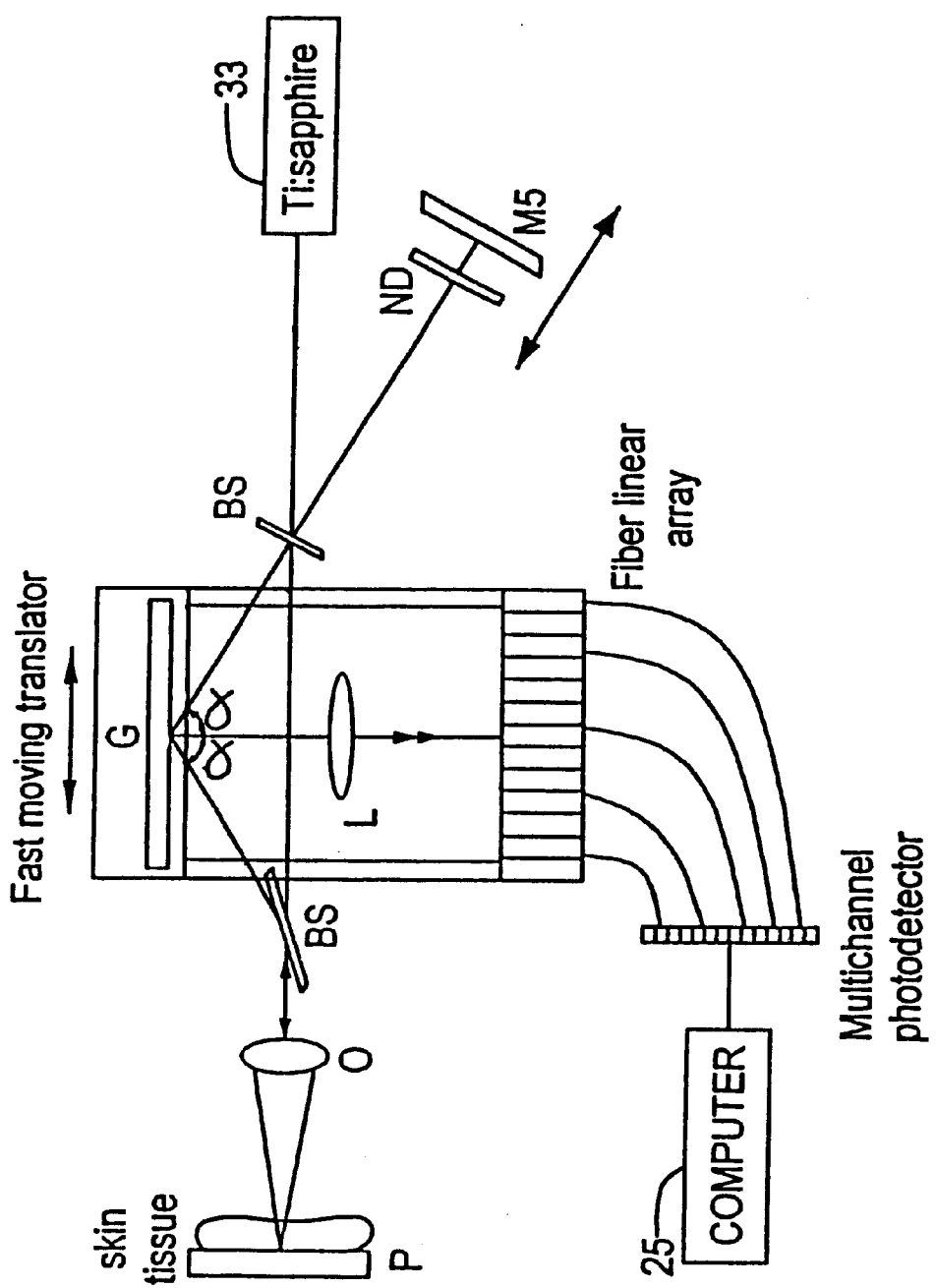
FIG. 18 is a schematic block diagram of a modification of the system shown in FIG. 17.

To simplify the multichannel photodetector LA and electronic detection system the diffraction grating and fiber linear array connected with the multichannel photodetector are mounted on a fast moving translator (see FIG. 18).

When the central wavelength ($\lambda$) of the laser source is discretely tuned the groove space p must satisfy the relation $p=\lambda/\sin\alpha$, where $\pm\alpha$ is the angle between reference (or signal) beams and normal to the diffraction grating. It can be performed using a composition of several co-plane diffraction gratings with different groove spacings (See FIG. 12). The vertical position of the composition grating is discretely changed by the Y translator to satisfy the relation (3)

Figure 20:
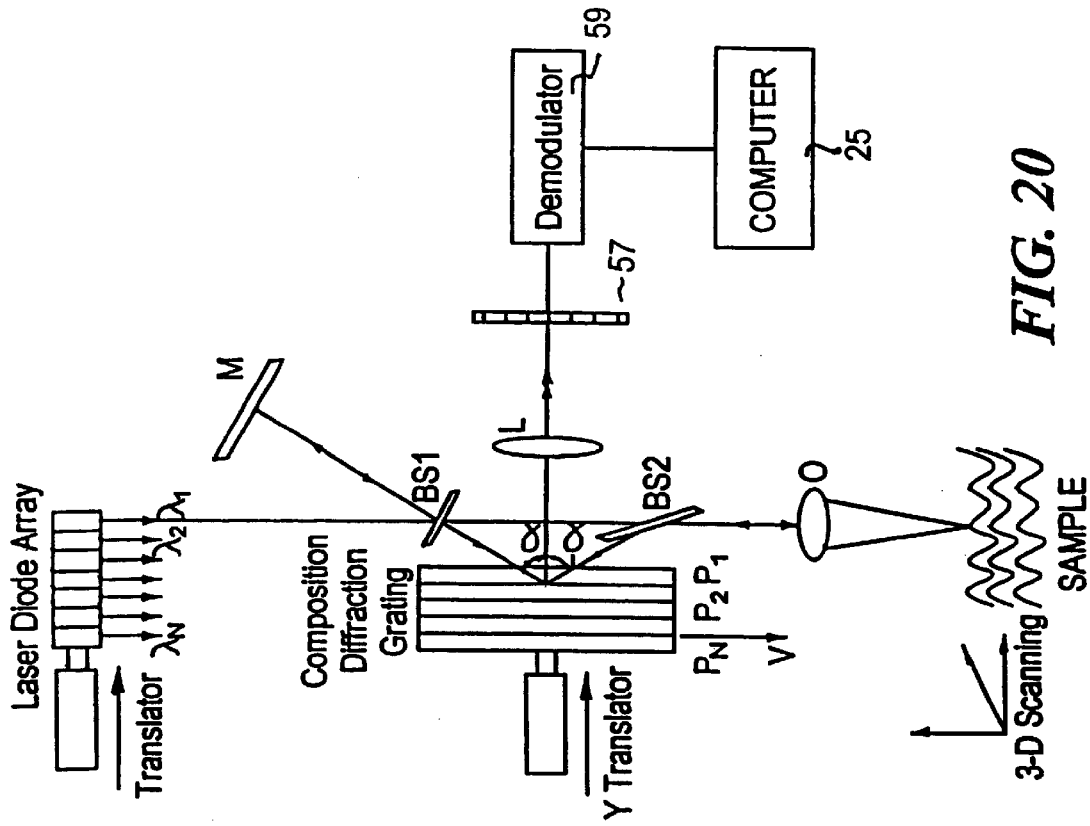
FIG. 20 is a schematic block diagram of a modification of the system shown in FIG. 11.
Figure 19:
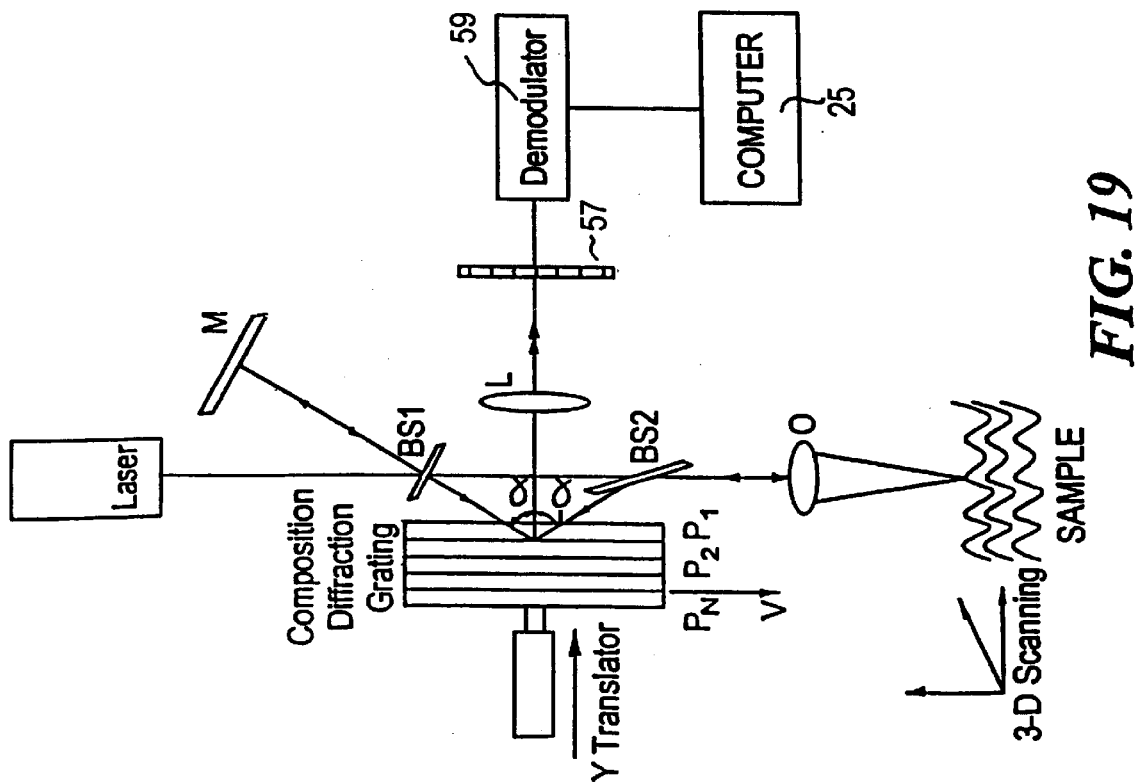
FIG. 19 is a schematic block diagram of a modification of the system shown in FIG. 11.

In another embodiment of the invention (see system 71 in FIG. 20), the light source one is an array of diode lasers LA, each emitting light at different wavelength $\lambda$, according to relation (2). The LA laser source is mounted on a holder, accommodating y (or x) translational stage. The position of one laser diode is synchronized with the position of one diffraction grating. The wavelength is selected for the maximum depth exposure typically from 600 to 1600 nm.

Figure 21:
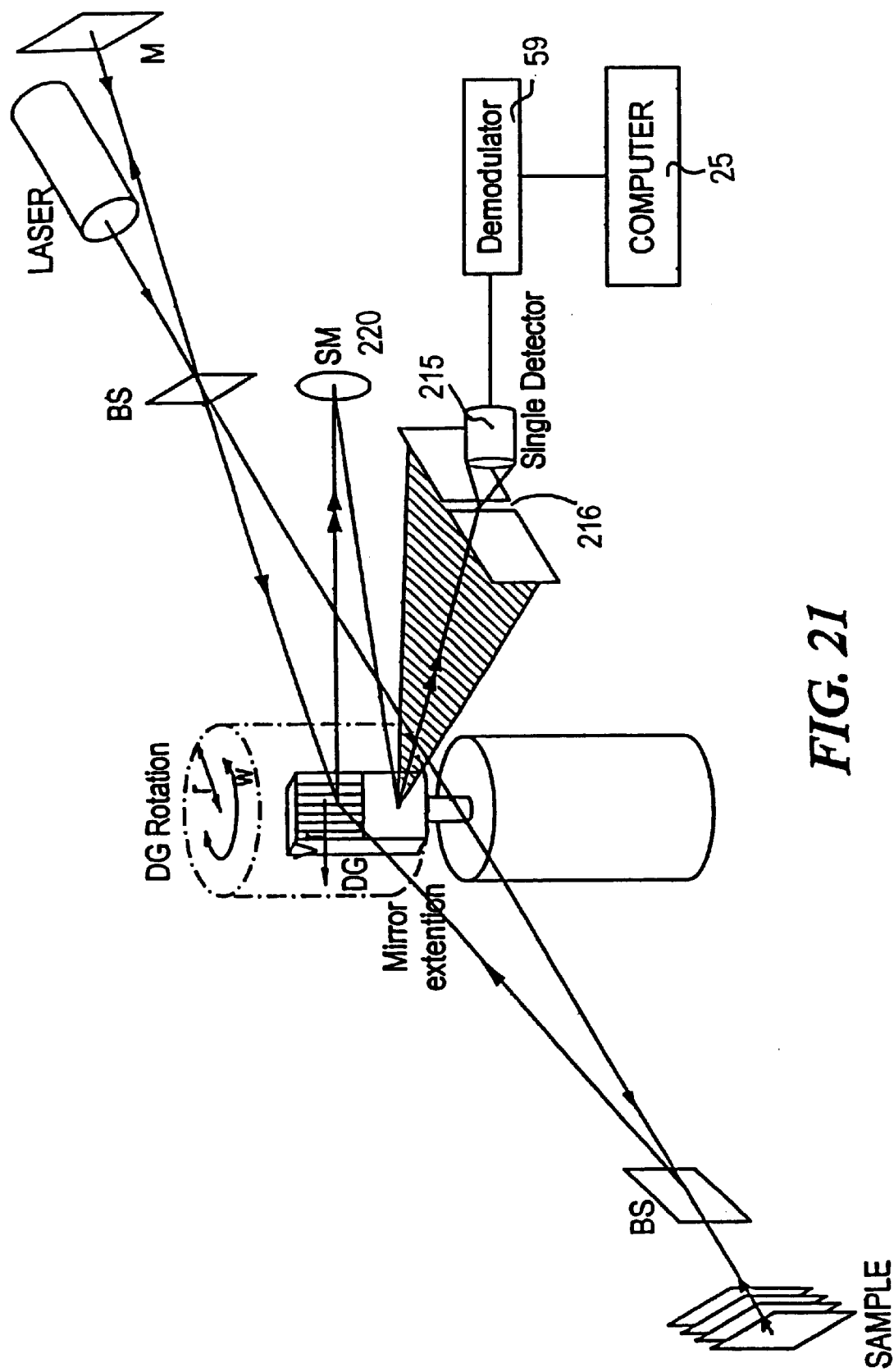
FIG. 21 is a schematic block diagram of a modification of another embodiment of a system for performing selected optical measurements of a sample constructed according to this invention.

To simplify the electronic detection system and to use a single detector 215 instead of a diode LA, a rotating diffraction grating DG with a vertical extension in the form of a reflecting mirror ME is used as shown in system 73 in FIG. 21. The diffracted beams are reflected from a stationary spherical mirror SM 220 which displaces these beams in the vertical direction and directs them back to the rotating reflection mirror ME. Beams reflected from rotating mirror ME are directed into a vertical slit VS 216. The slit plane is optically conjugated with the grating plane by the reflecting spherical mirror SM 220. Optical signal passing the slit is detected by demodulating the single detector output at the Doppler shift frequency between signal and reference beams produced by rotating grating RG.

Figure 22:
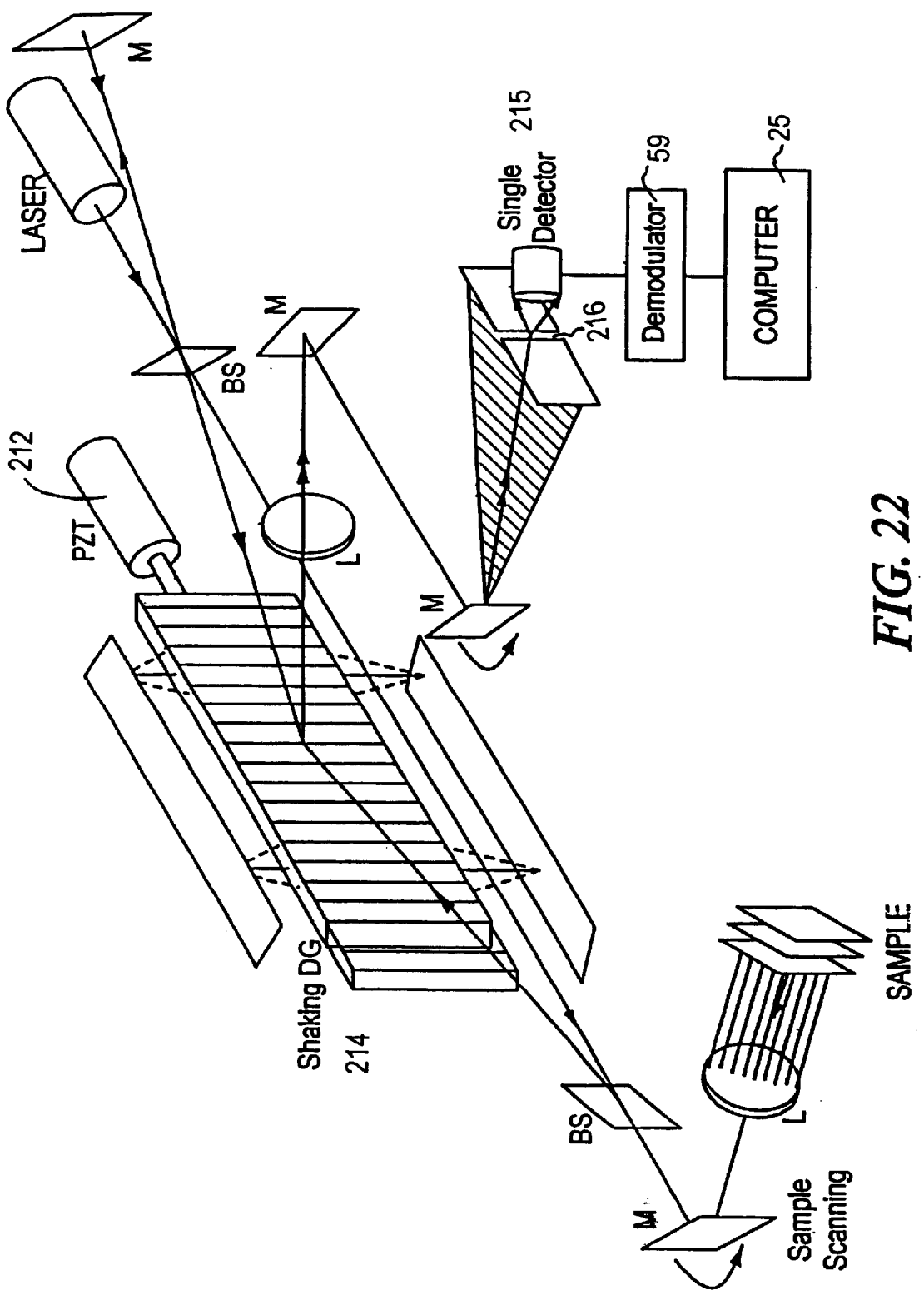
FIG. 22 is a schematic block diagram of a modification of the system shown in FIG. 21.

To simplify the mechanical system using a PZT shaking grating DG 214, the diffracted signal and reference beams are reflected from a small angle shaking reflection mirror SRM as shown in system 75 in FIG. 22.

Figure 23:
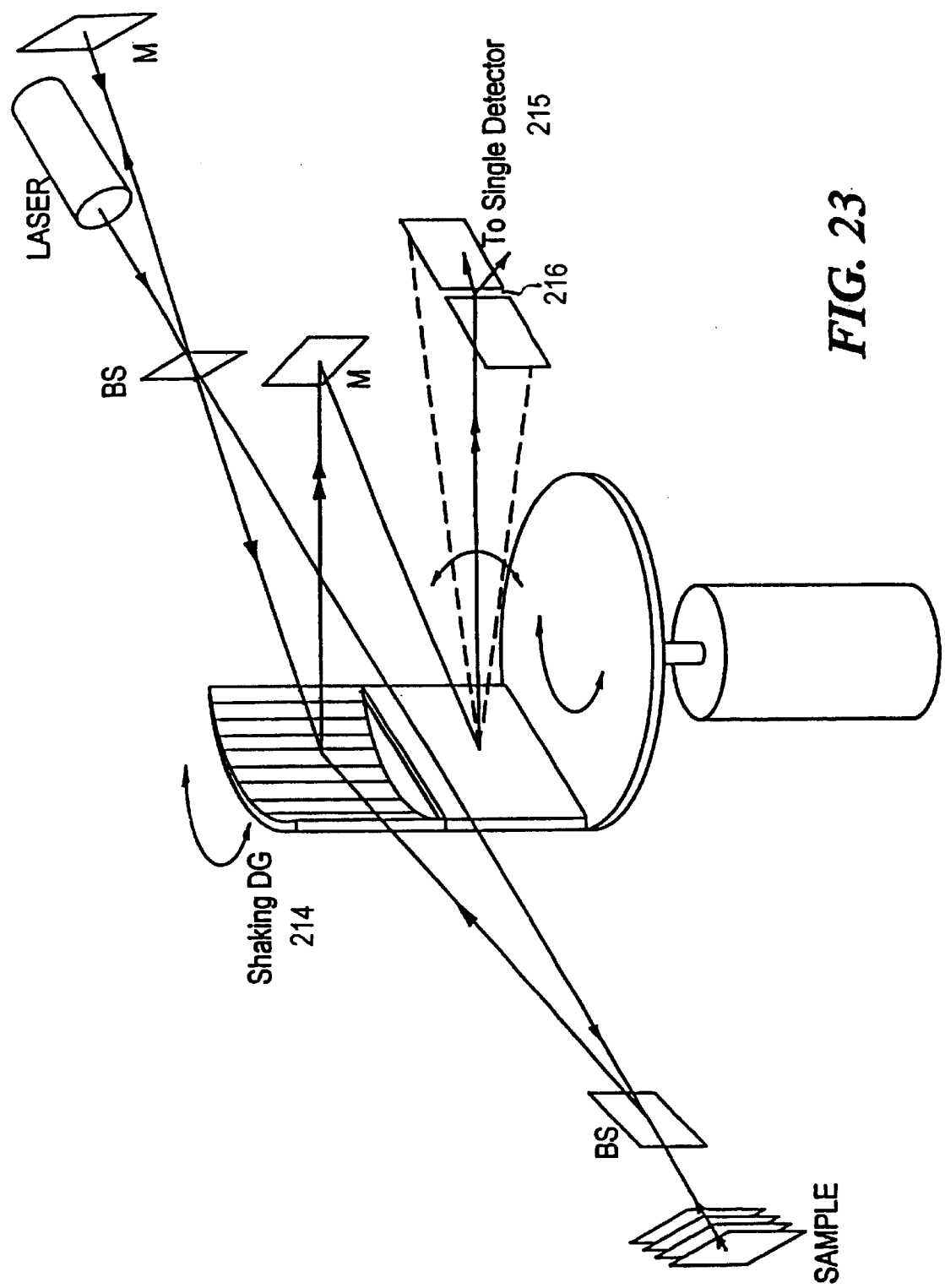
FIG. 23 is a schematic block diagram of a modification of the system shown in FIG. 22.

To increase the SRR without additional diffraction gratings one can use a small angle shaking mechanism SASM for shaking the diffraction grating which is carried on a spherical (or cylindrical) reflection surface with the vertical extension by the reflecting mirror. The axes of a small angle shaking are passing through the center of the grating spherical (or cylindrical) reflection surface (see FIG. 23).

Figure 24:
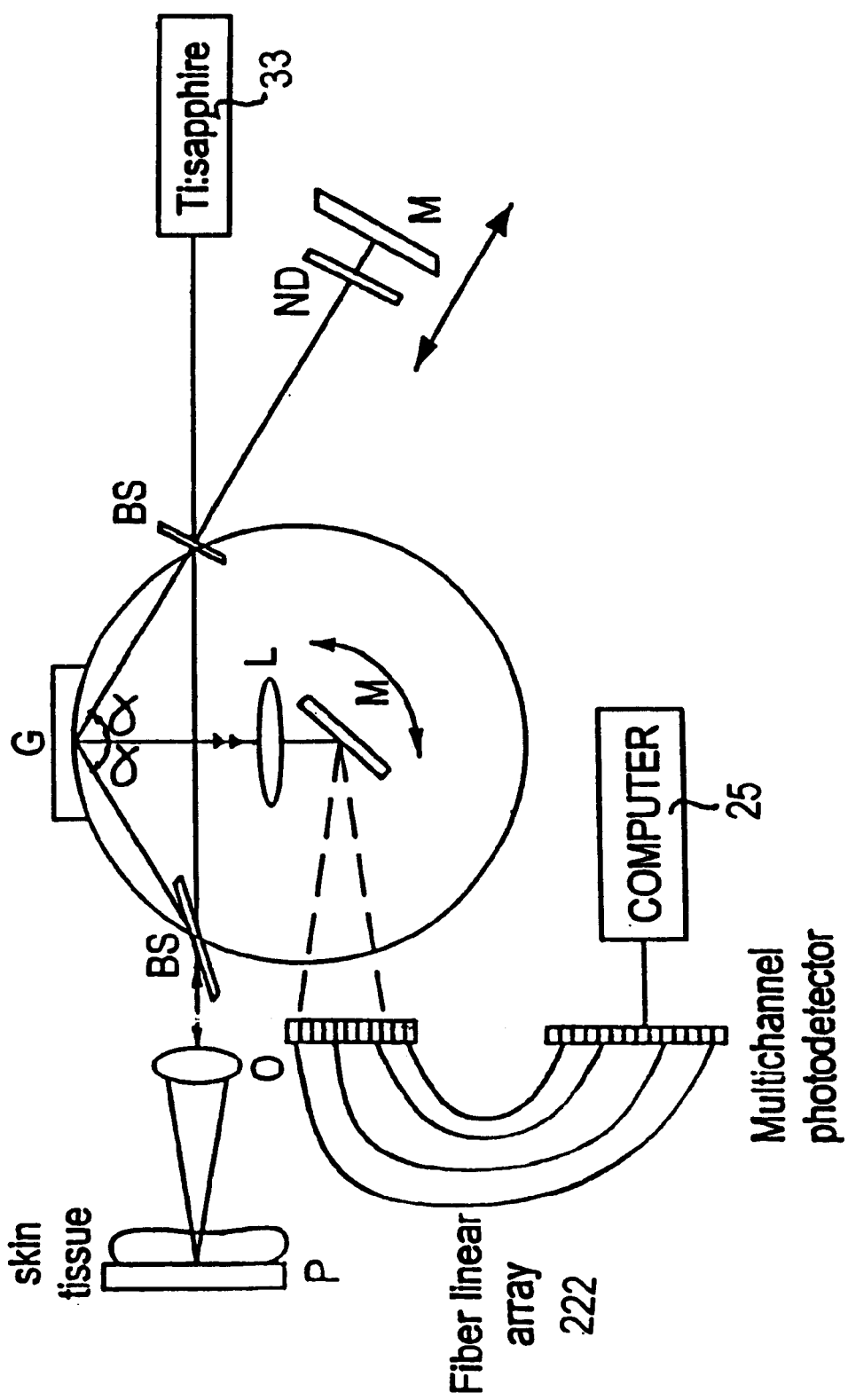
FIG. 24 is a schematic block diagram of a modification of the system shown in FIG. 23.

To increase the data acquisition speed the interferometric system can be performed so that beams reflected from the shaking (or rotation) grating are directed to the shaking (or rotation) reflection mirror SRM placed at the axes of shaking (or rotation) of the grating and after mirror reflection are directed to a stationary fiber array 222 connected with the multichannel photodetector (see system 77 in FIG. 24).

Figure 25:
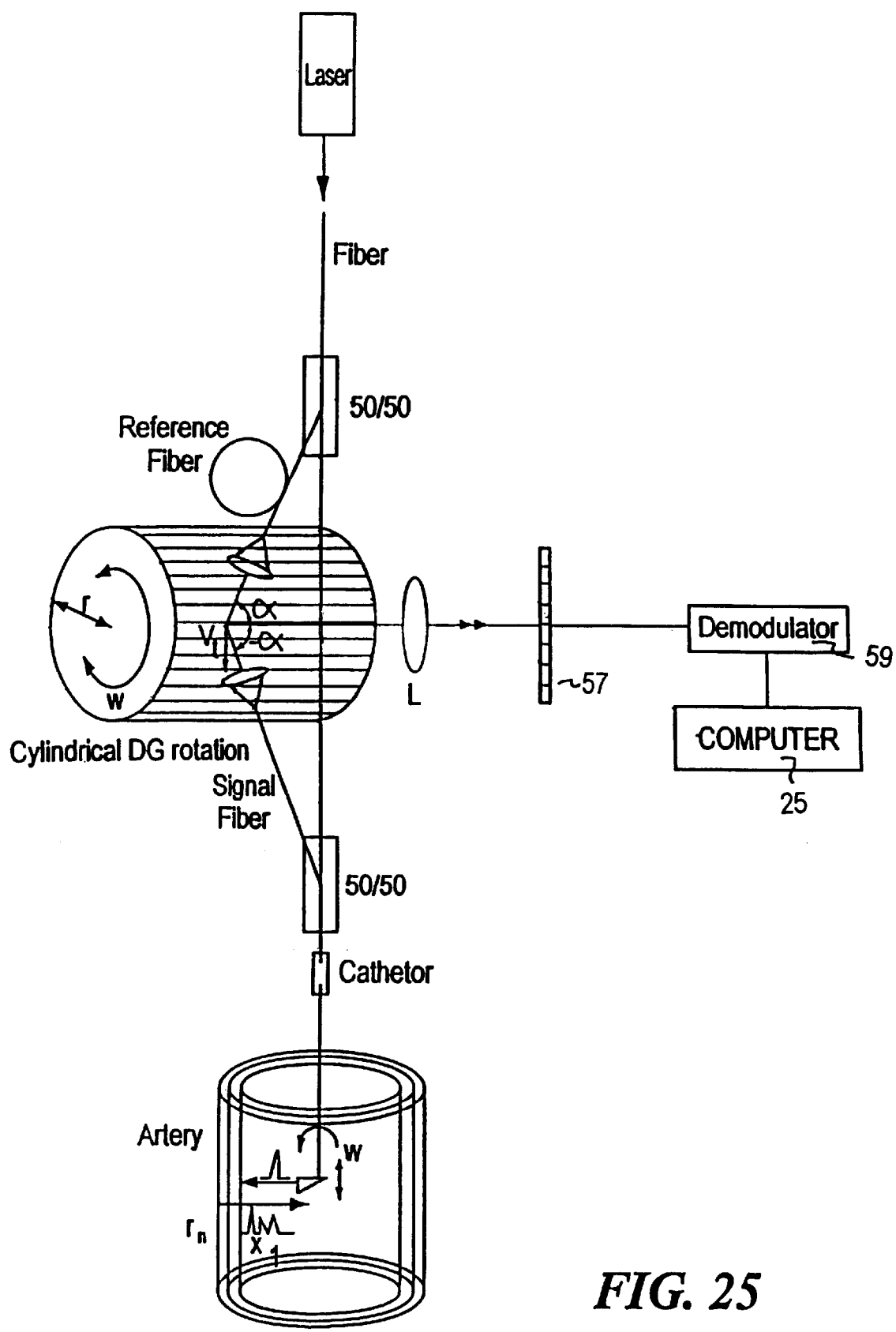
FIG. 25 is a schematic block diagram of a modification of the system shown in FIG. 16.

To obtain an image of the surface structure of the human internal organ, such as artery cross section, tissue section or mucous the signal and reference interferometer arms are fiber-coupled as shown in system 79 in FIG. 25. Tissue reflectance is obtained axially by the grating-generated depth scan and digitizing the magnitude of the demodulated interference envelope. The input of the signal beam fiber is connected with a catheter and the fiber output is connected with a lens LEI which directs the signal beam to the grating at the diffraction angle a. The fiber output of the reference beam is connected with a lens LE2 which directs the reference beam to the grating at the diffraction angle $-\alpha$. Fiber optics allow to improve the flexibility of the interferometer set up. The catheter is designed to scan the beam in a circumferential pattern to image cross sectionally through the vessel (or other biological structure) into which it is inserted. During image acquisition the catheter is inserted into the tissue structure being imaged (the artery or other internal tissue channel), and, as the drive motor (not shown) turns, the shaft of the catheter and the distal optics circumferentially scan the focused beam perpendicular to the axis of the catheter. An image is acquired as the beam angle of rotation is varied over some range (usually 360 deg). The speed of imaging depends on the speed of the rotation and the proposed interferometer acquisition speed.

Figure 26:
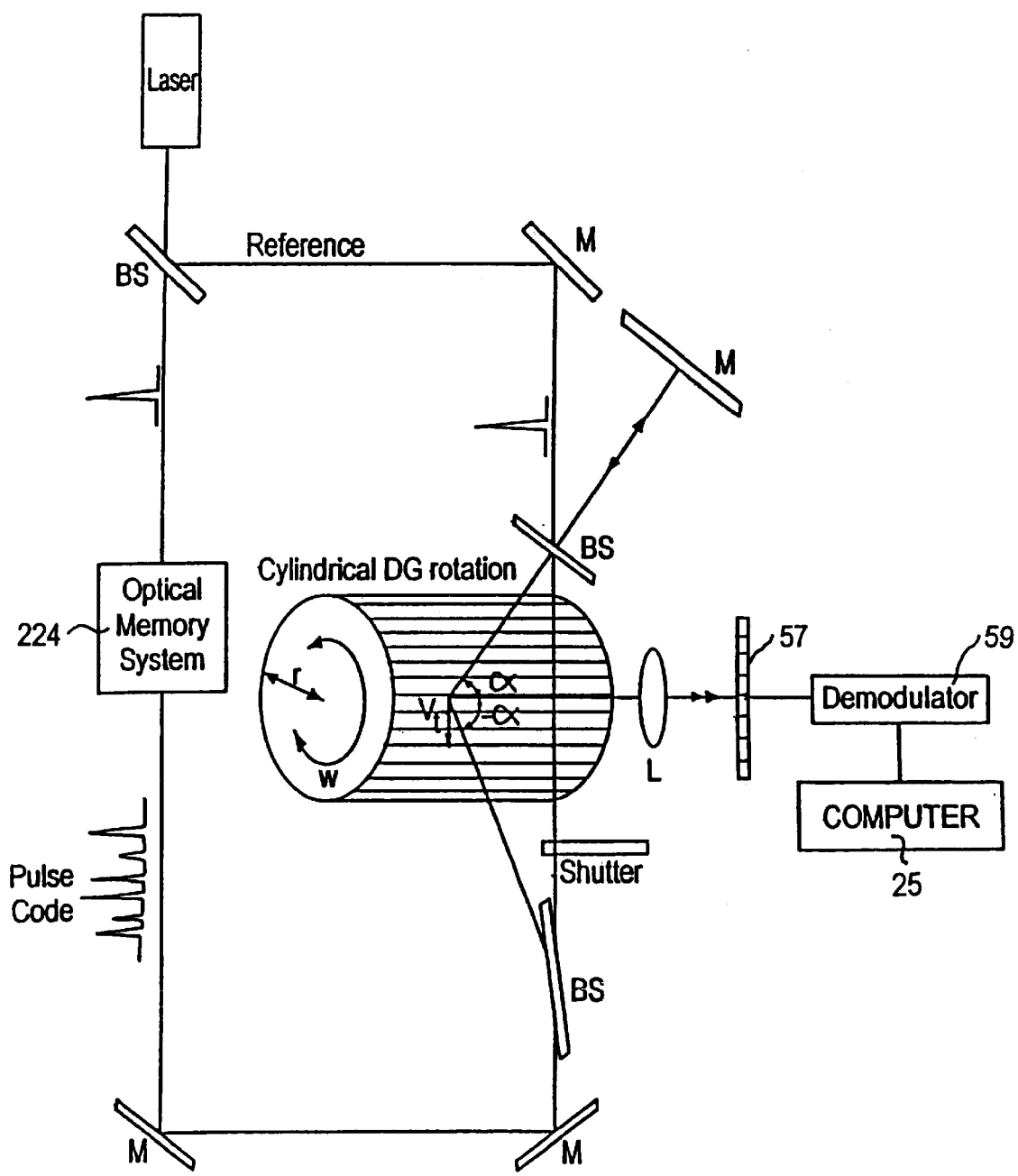
FIG. 26 is a schematic block diagram of a modification of the system shown in FIG. 16.

This interferometric system can be used for optical communications as a receiver of a pulse code signal, retrieved from an optical memory system 224, for example, hole-burning holography (see system 81 in FIG. 26). In the case of the time-domain optical data storage one must detect signal beams despite the presence of relatively strong readout beams in close temporal and spatial proximity. The presence of strong readout beams can be turned to an advantage by use proposed technique. Our approach eliminates the need to ensure overlap between tightly focused and angled excitation beams and the need for optical shutters to prevent detector saturation by intense excitation beams. Other advantages include the ability to minimize cross talk between adjacent spatial storage cells and the ability to amplify signals sufficiently to overcome noise levels of photodiode-based detection system. A pulse code signal is directed on the grating at the diffraction angle a and a coherent reference pulse is directed on grating at the diffraction angle $-\alpha$. For time-display window of 20 ps and the pulse amplitude correlation time of 100 fs the pulse code has about $2 \cdot 10^3$ bit. The information reading speed of $2 \cdot 10^9$ bits/s with 1 MHz repetition rates for 1 $\mu$s axial scan time response. The SNR is about 100 dB.

Due to economic advantages, maturing technology, and high information capacity, single-mode fiber-optic transmission media will be embedded in future telecommunications networks. A desirable feature for these future optical networks would be the ability to process information directly in the optical domain for purposes of multiplexing, demultiplexing, filtering, amplification, and correlation. Optical signal processing would be advantageous because potentially it can be much faster than electrical signal processing and because it would obviate the need for photon-electron-photon conversion.

Figure 27:
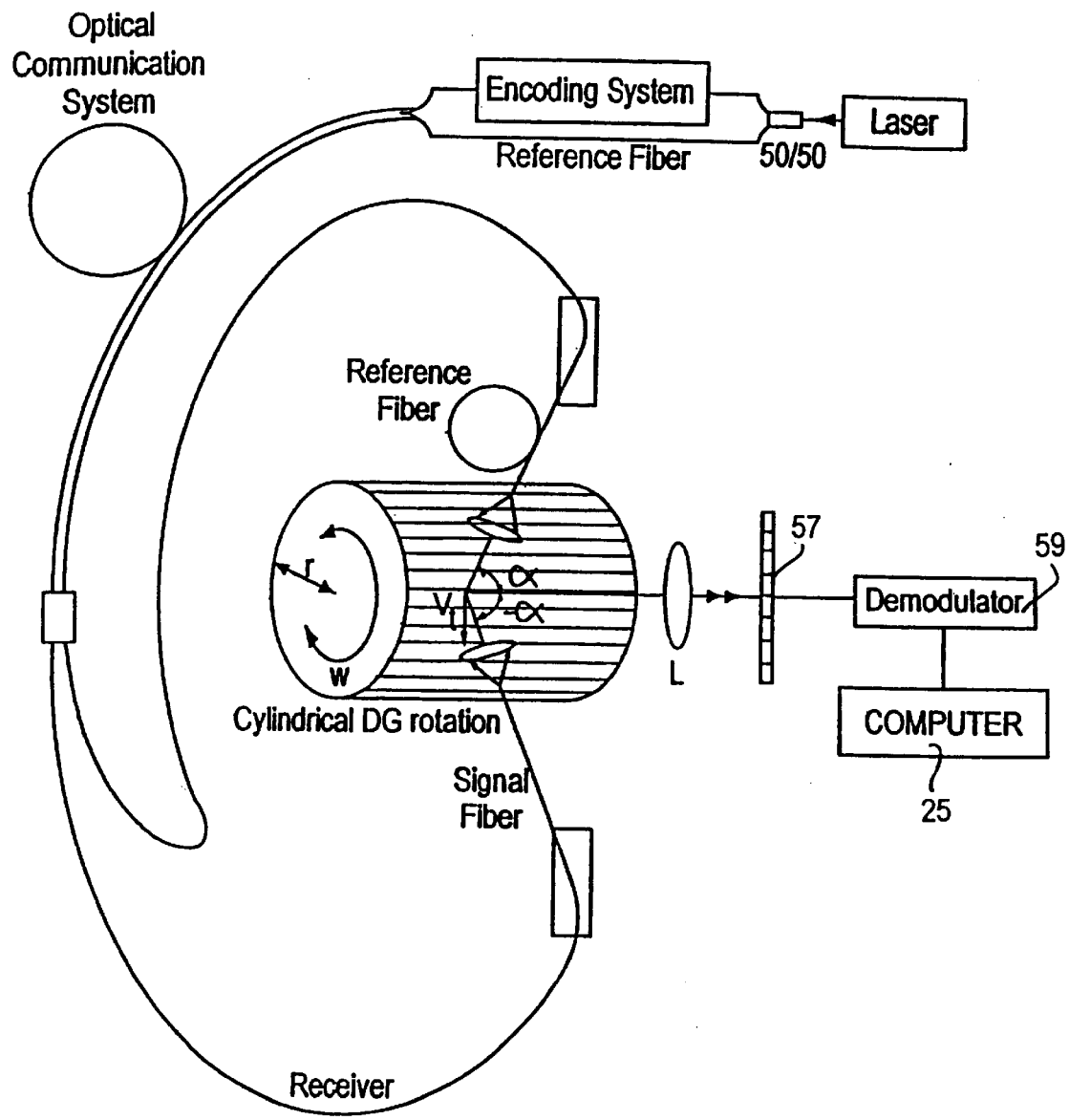
FIG. 27 is a schematic block diagram of a modification of the system shown in FIG. 16.

Characterization of weak ultrashort intensities is essential for single-event detection for time-domain communications. Ultrafast time-domain data packets can be created by the filtering of mode-locked laser pulses. Efficient detection of ultrashort time-domain signals requires novel receiver systems. The proposed interferometer can be performed as a receiver of a pulse code signal, received from the optical communication system (OCS) (see system 83 in FIG. 27). The pulse code signal is directed on the grating at the diffraction angle a and coherent reference pulse extracted from OCS is directed on grating at the diffraction angle $-\alpha$.

Figure 28:
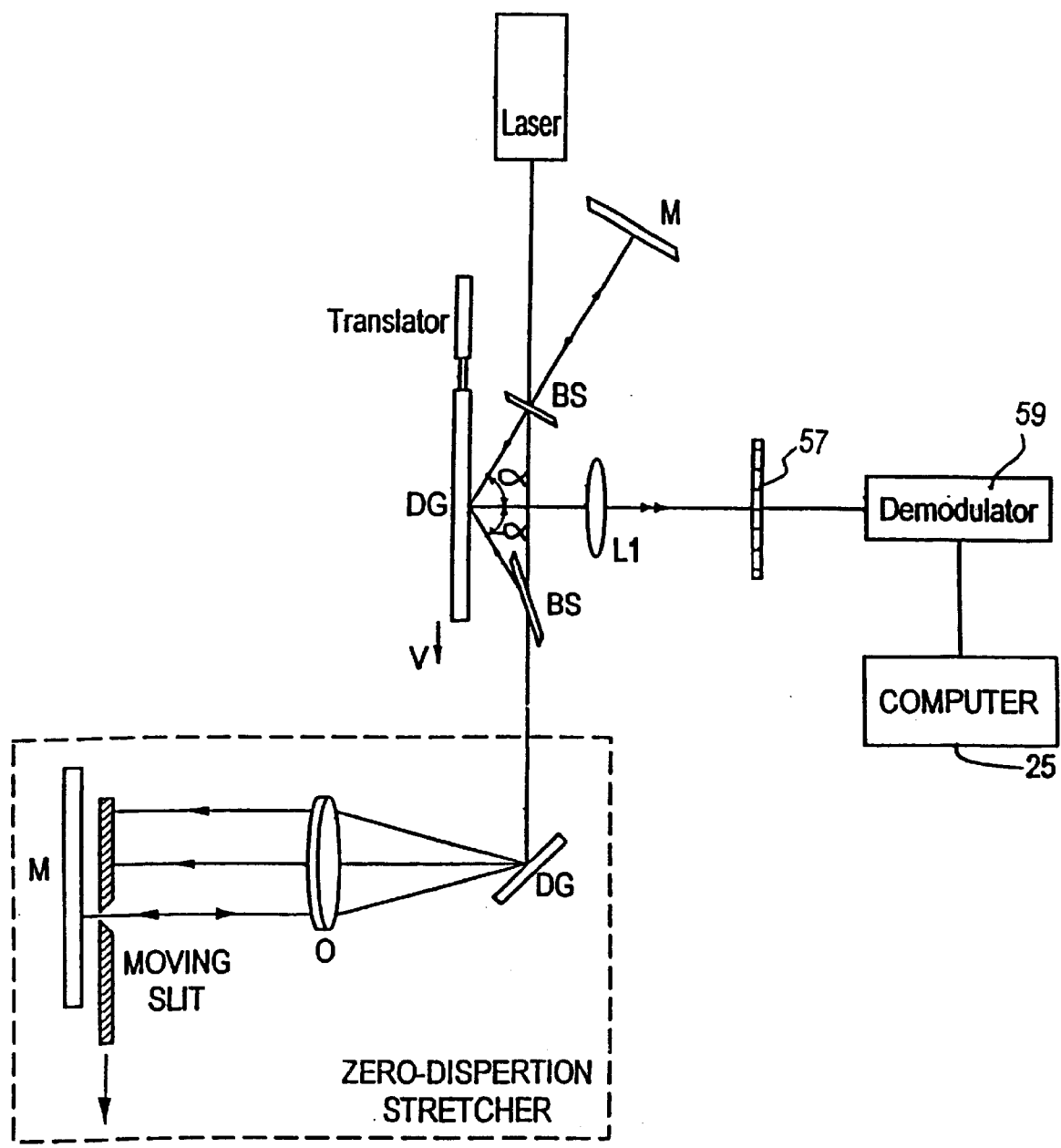
FIG. 28 is a schematic block diagram of a modification of the system shown in FIG. 16.

The development of sub-picosecond laser sources has largely precluded techniques for accurate and complete characterization of pulses coming from such lasers. Today the most commonly used measurement is the nonlinear autocorrelation. While this technique generally require high intensity pulses. The spectral phase of femtosecond pulse can be measured using a frequency domain correlator. This technique involves cross correlating different spectral slices of the original pulse with itself. The relative delay of the spectral components with respect to each other provides information about any chirp which may be present. The interferometer can be performed so that signal beam includes zero-dispersion stretcher with moving slit placed in the stretcher spectral plane to measure dependence of the output signal position on the slit position (see system 85 in FIG. 28). These measurements allow a person to obtain the spectral phase of the input pulse increasing measurement sensitivity and acquisition speed.

Figure 29:
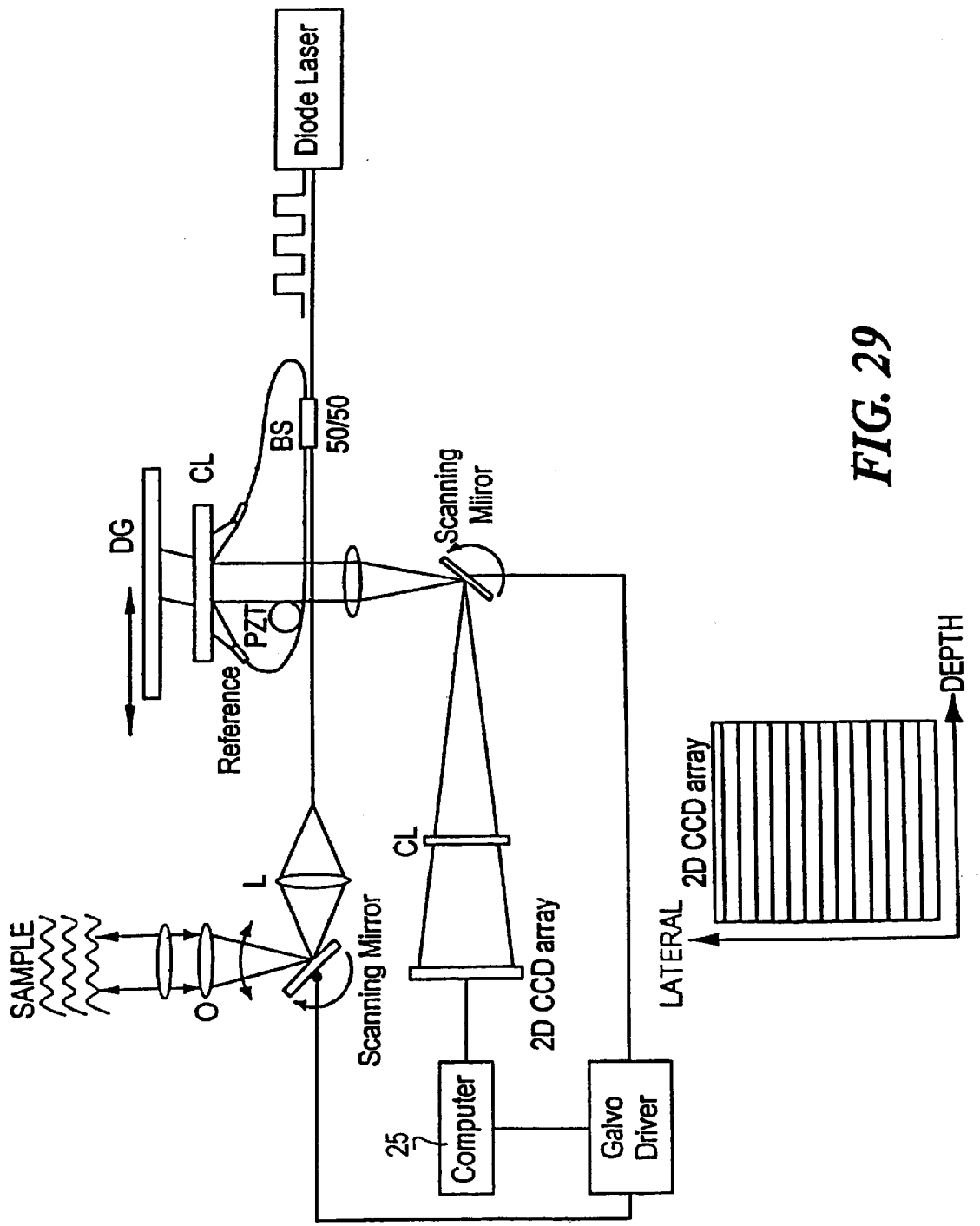
FIG. 29 is a schematic block diagram of another embodiment of the invention.

In system 91 shown in FIG. 29 signal and reference beams are focused by the combination of the cylindrical lenses into the narrow line on the surfaces of a grating and the 2D CCD array. Position of this narrow line is changed on the CCD array, for example, in vertical direction by a rotating mirror so that each lateral position of the signal beam produces the vertical shifted narrow line image on the CCD array. Several depth-lateral digital images are recorded with different phase shifts. These images are digital processing to produce a 3D image.

Figure 30:
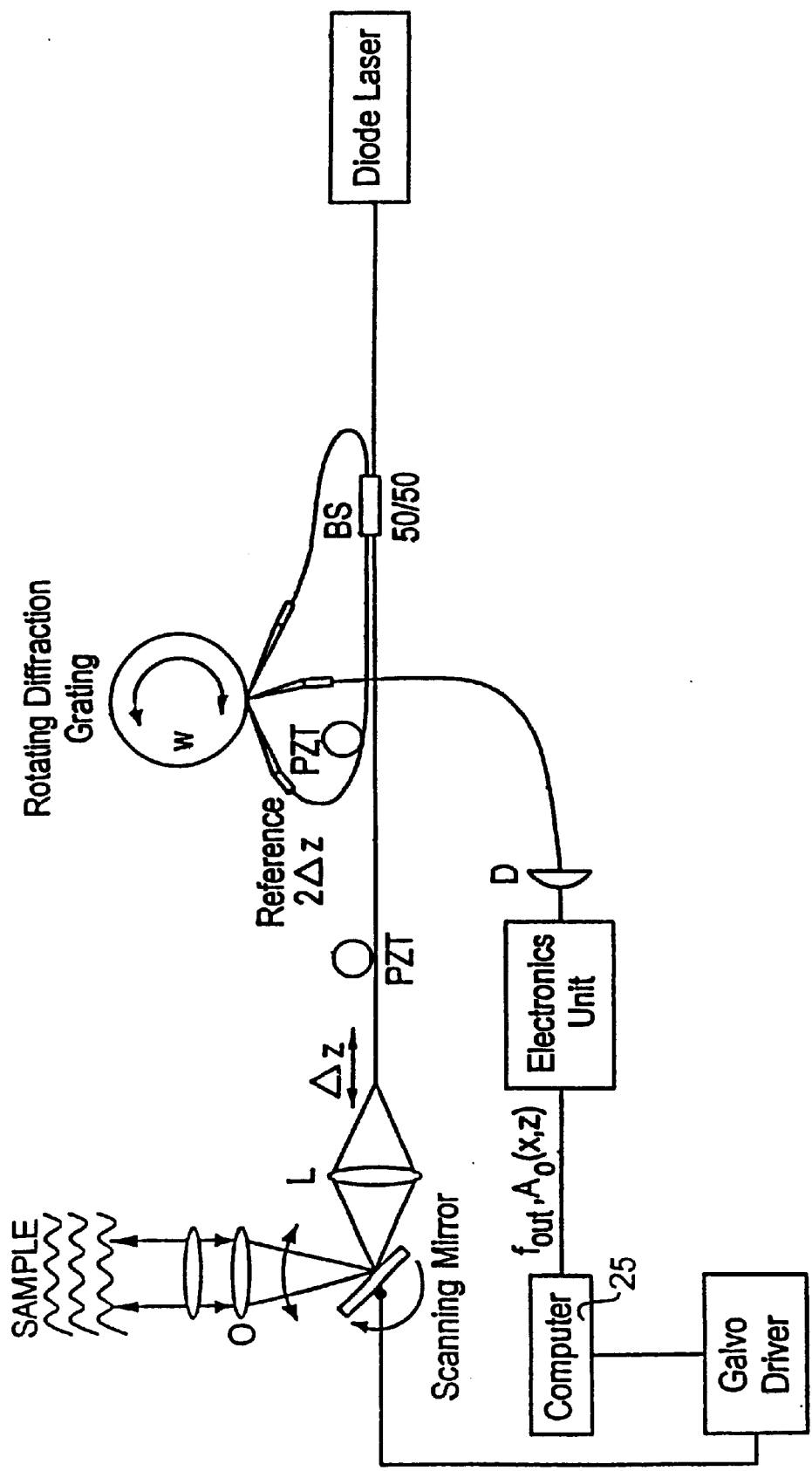
FIG. 30 is a schematic block diagram of another embodiment of the invention.

In system 99 shown in FIG. 30, the signal to noise ratio is increased using an interferometric system wherein the signal and reference beams are focused into a diffraction grating. The optical output signal is detected by demodulating the single detector output at the Doppler shift frequency.

In another embodiment of the invention (not shown) the interferometric system is constructed so that a linear source image on the surface of the sample can be rotated, for example, by 90 degrees. A PZT stretched fiber is inserted to produce phase modulation. Several depth-lateral digital images are recorded by a 2D imaging CCD array with different phase shifts. These images are digital processing to produce a 3D image of the internal structure of a sample.

In another embodiment of the invention (not shown) two perpendicular linear sources illuminate a sample simultaneously. Two diffraction gratings with perpendicular orientations of the grooves are used to create simultaneously two images on two CCD arrays to produce signals for a 3D image processing of the internal structure of a sample.

In another embodiment of the invention (not shown) two orthogonal gratings placed at same or different locations, one or two CCD arrays are used to produce images in x or y directions in combination with the axial z scans of the depth of a sample along the grating dispersion. The images produced by the CCD arrays are used to create a 3D image of a sample.

Figure 31:
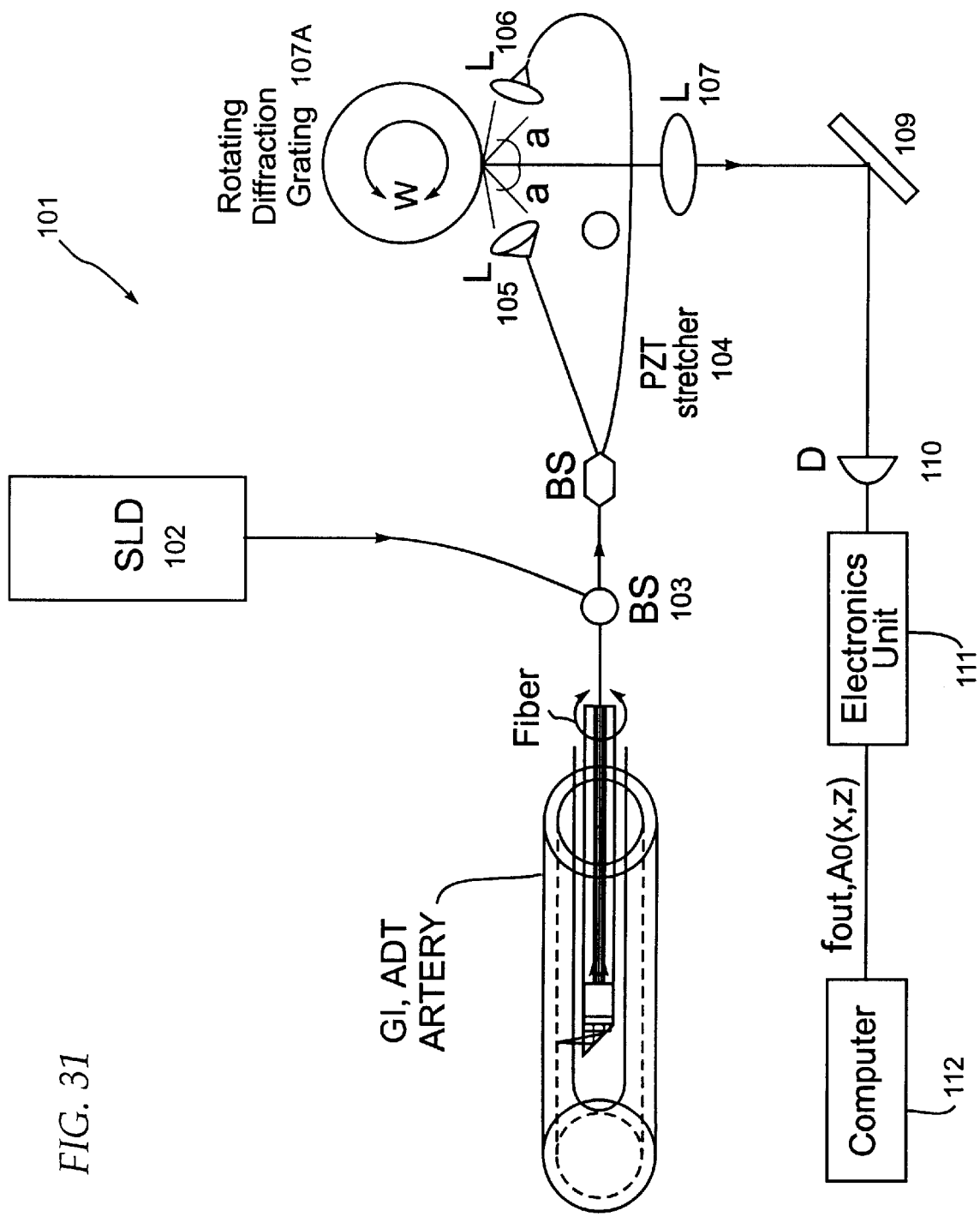
FIG. 31 is a schematic block diagram of another embodiment of the invention.

In FIG. 31 there is shown another embodiment of the invention identified by reference numeral 101. System 101 includes an SLD light source 102, a pair of beamsplitters 103 and 104, three lenses 105, and 106 and 107, a rotating diffraction grating 107a, a stretcher 108, a mirror 109, a detector 110, electronics 111 and a computer 112.

Figure 32:
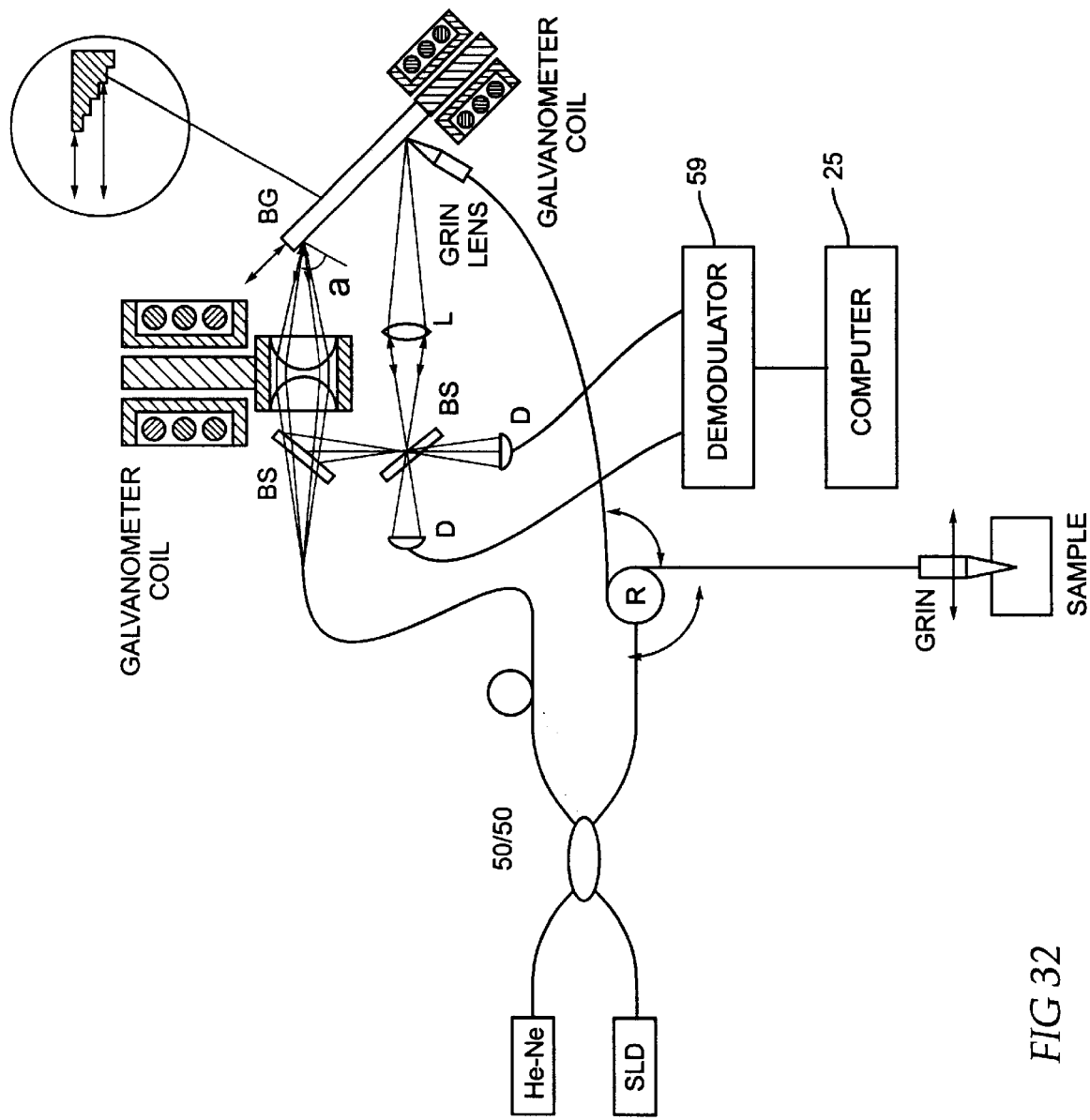
FIG. 32 is a schematic block diagram of another embodiment of the invention.
Figure 33:
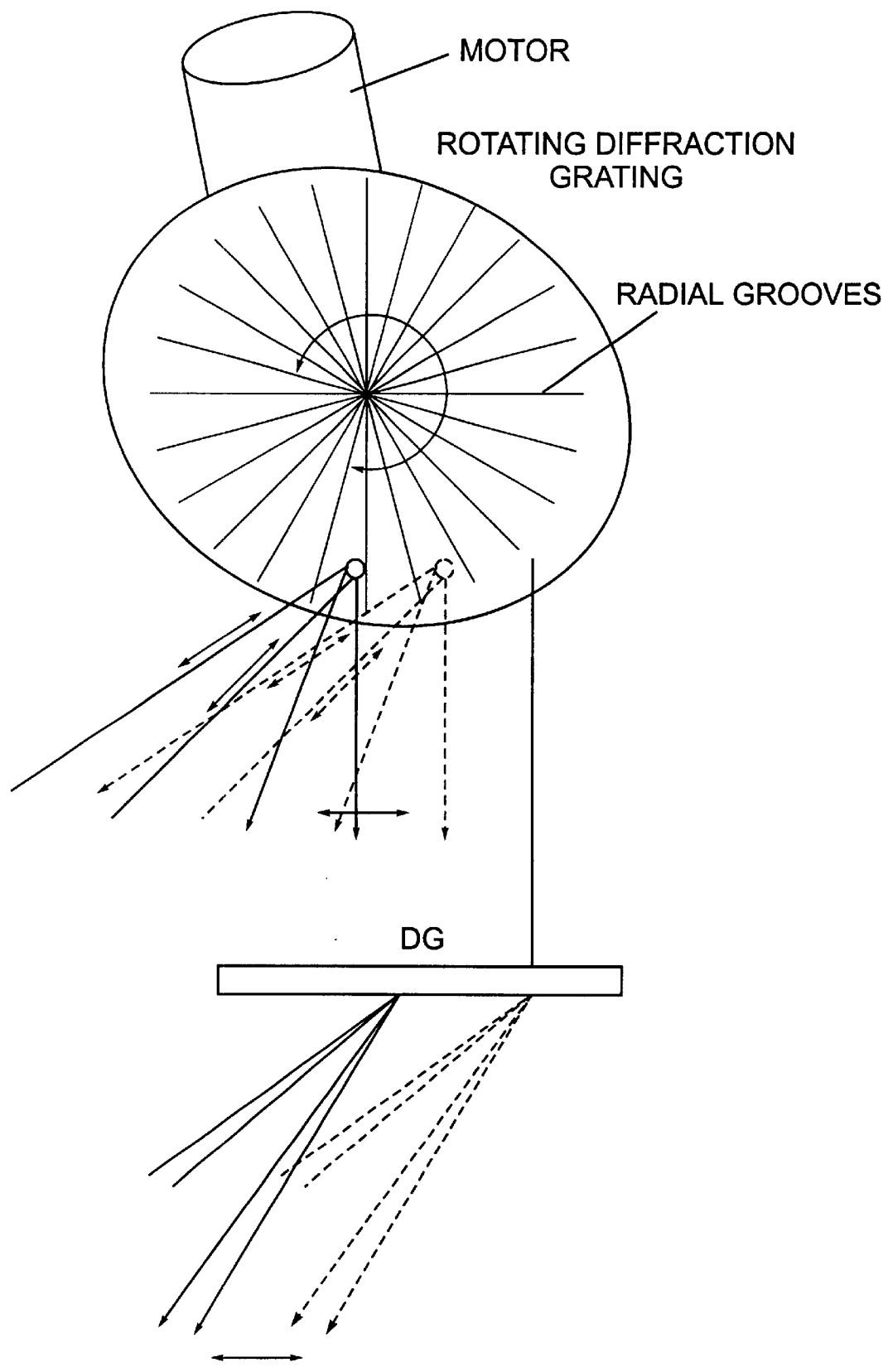
FIG. 33 are views of the diffraction grating in the embodiment shown in FIG. 32.

A further embodiment of the invention is shown in FIG. 32 and a view of the diffraction grating in the system in FIG. 32 is shown in FIG. 33.

Figure 34:
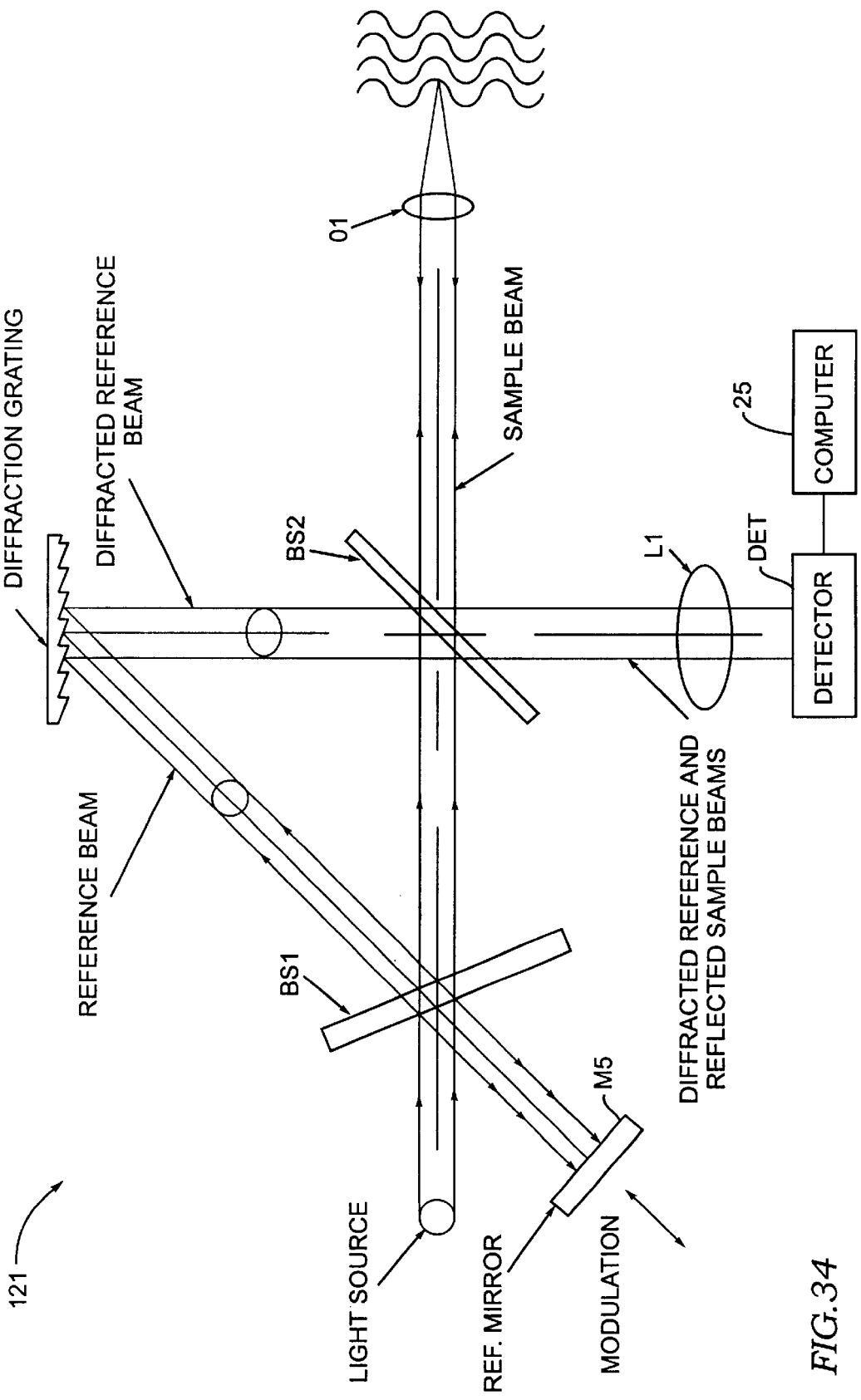
FIG. 34 is a schematic block diagram of another embodiment of the invention.

In FIG. 34 there is shown another embodiment of the invention identified by reference numeral 121. In this embodiment, a diffracted reference beam is combined with reflections from a sample.

In system 121 light from source 123 strikes a first beamsplitter BS1 where it is split into a transmitted part and a reflected part. The reflected part is reflected off reference mirror M5. Reflected light from mirror M5, which constitutes a reference beam, passes back through beamsplitter BS1 and strikes diffraction grating DG. The transmitted part of the light passing through beamsplitter BS1 passes through beamsplitter BS2 and is brought to focus by a lens 01 onto sample S. Diffraction grating DG is angled relative to the reference beam so that one of said first or second or higher diffraction orders from the light strikes the diffraction grating DG. The diffracted order that is normal to diffraction grating DG, identified in the FIG. as the diffracted reference beam, is combined with reflections from sample S by a second beamsplitter BS2. The combined beam is brought to focus into detector DET by a lens L1. The output of detector DET is fed into a computer COMP.

Figure 35:
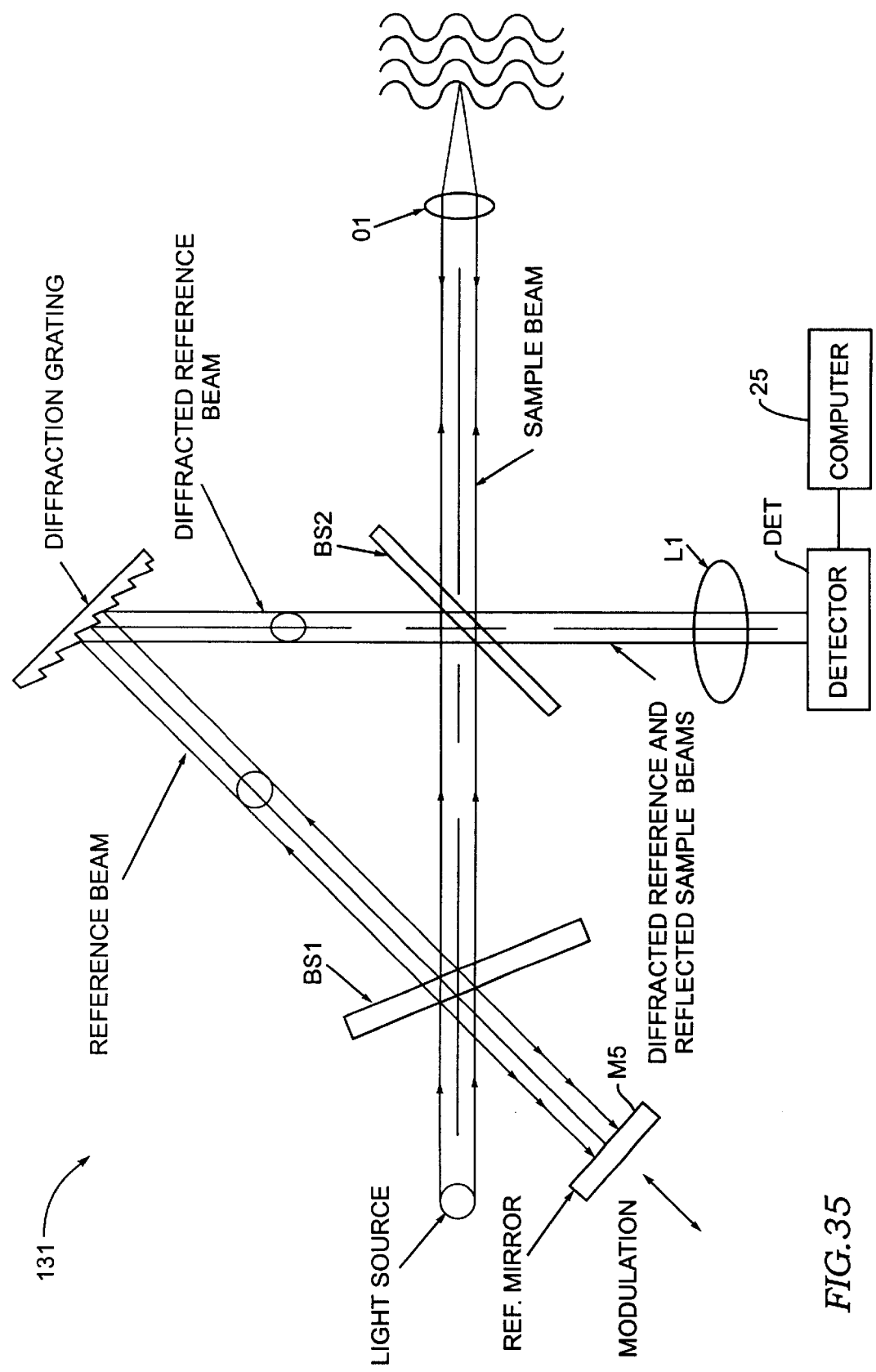
FIG. 35 is a schematic block diagram of another embodiment of the invention.

In FIG. 35 there is shown another embodiment of the invention identified by reference numeral 131. System 131 differs from system 121 in that diffraction grating DG is angled relative to the reference beam such that the reference beam is normal to the diffraction grating DG and the diffracted reference beam (either the first, second or higher order, and either positive or negative) that is combined with reflections from the sample is not normal to diffraction grating DG.

Figure 36:
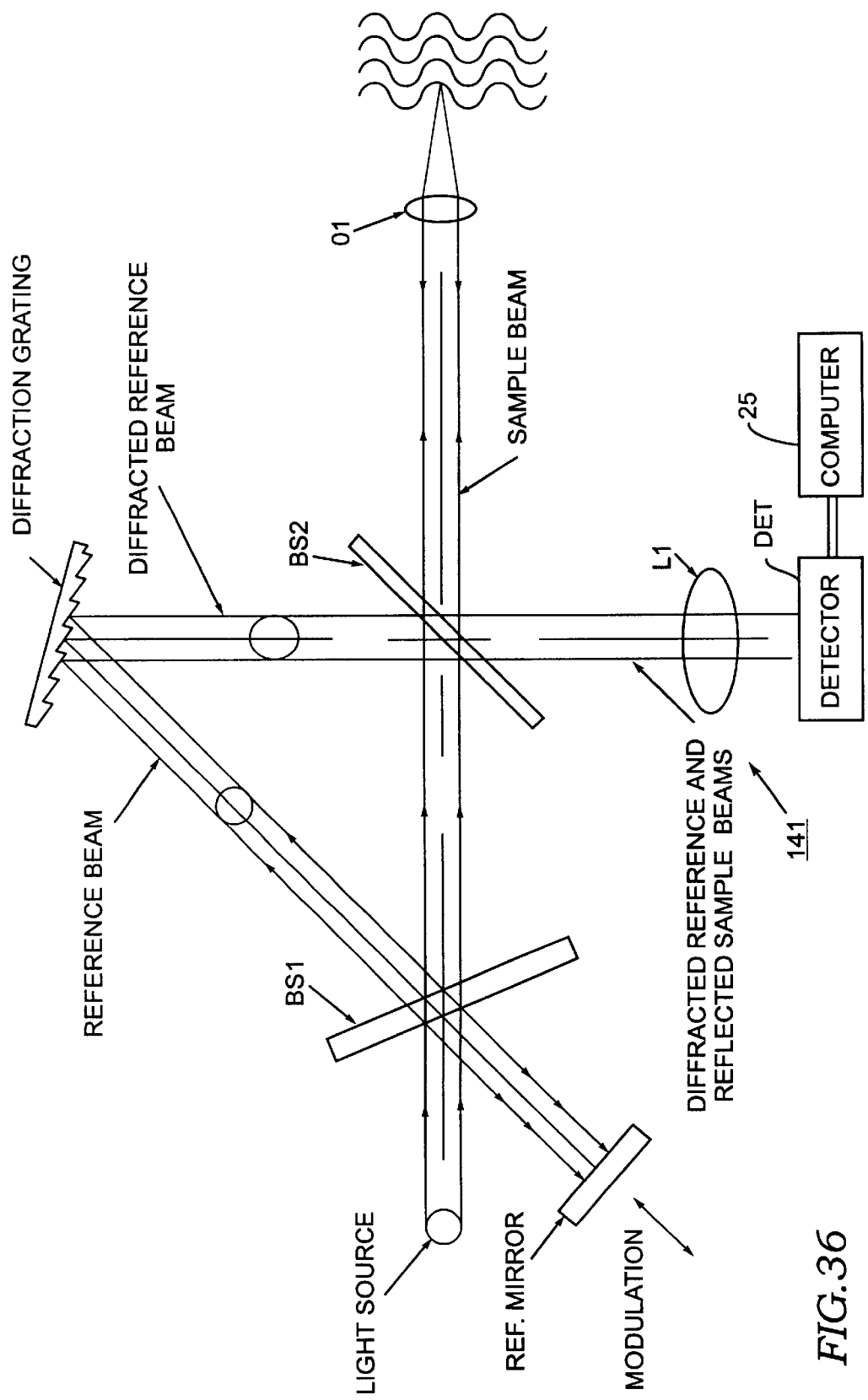
FIG. 36 is a schematic block diagram of another embodiment of the invention.

System 131 shown in FIG. 36 differs from system 121 in that the reference beam is not normal to diffraction grating DG.

Figure 37:
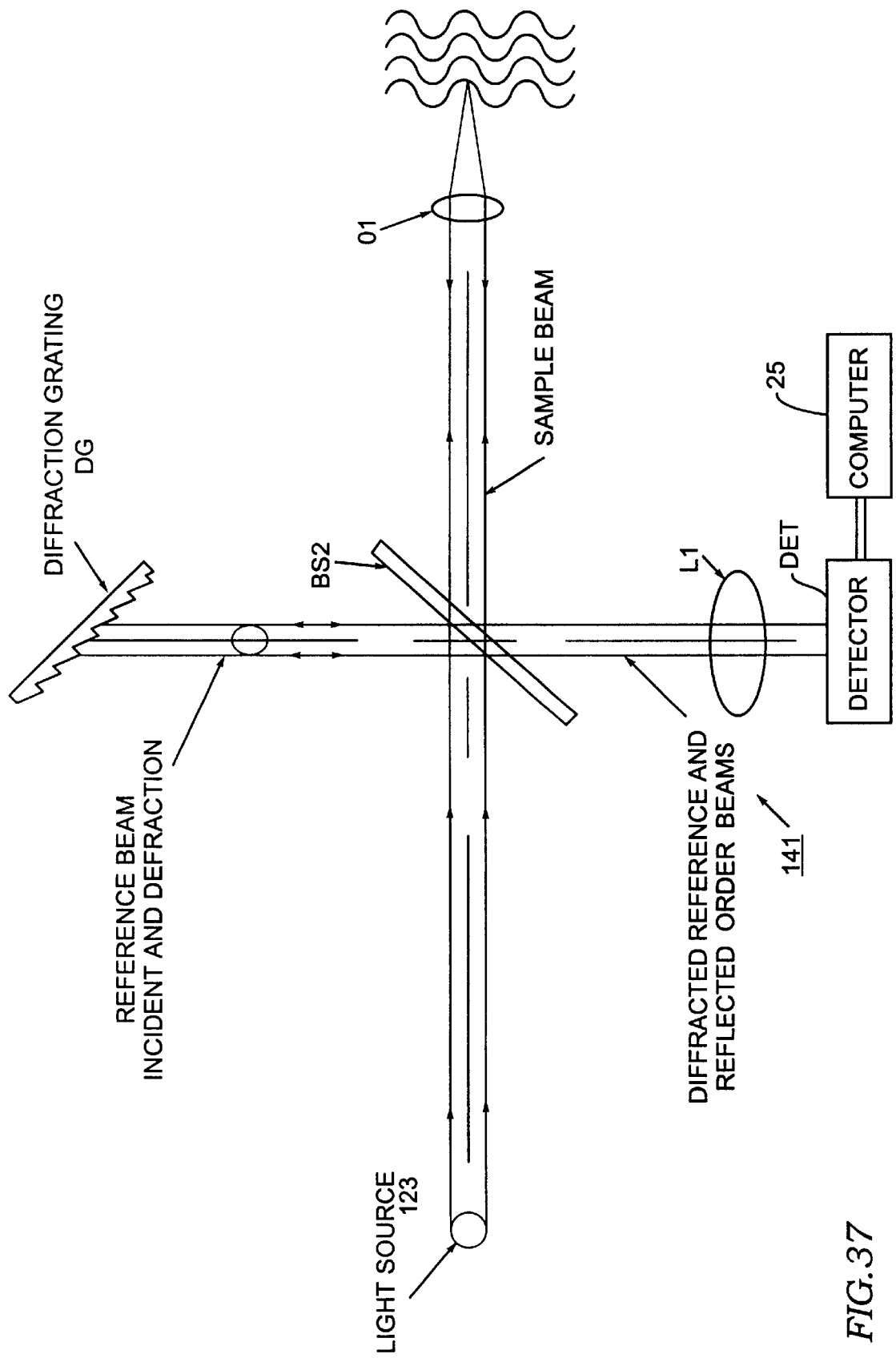
FIG. 37 is a schematic block diagram of another embodiment of the invention.

System 141 shown in FIG. 37 differs from system 131 in that the first beamsplitter BS1 and the reference mirror M5 are eliminated. Instead, beamsplitter BS2 is used to produce a reference beam which strikes diffraction grating DG to produce a diffracted beam which is combined with reflections from the sample beam and sample beam which strikes the sample. The reference beam is angled relative to the diffraction grating DG. The diffracted reference beam may be a first, second or higher order, either positive or negative, which coincide in a Littrow mode.

Important features of this invention include the following:

1. The use of diffraction grating to time resolve reflected signals from material by interference with reference pulse in ± first (or higher) diffraction orders.

2. The use of a time resolved interference method to obtain the depth map information for reflected signals from layers and defects in scattering medium.

3. The use of a time resolved interference method for a depth scan to obtain a depth map of a scattering medium below its surface up to 3 mm from the reflections within that region.

4. The use of a time resolved interference method for depth analyses of a tissue, semiconductor structure, art work on biological objects within a few mm depth. For tissue analyses it can be used to detect histological changes in tissue and artery wall such as plaque, fat, atheroscleroses.

5. A single-shot correlation-domain interferometric system using a grating-generated coherent depth scan interferometer and a broad-band laser source. The positive and the negative first-order diffracted signal and reference beams propagate along the normal to the grating. The diffraction grating introduces a continuous optical delay between the reference pulses and pulses reflected by the sample in the direction of the grating dispersion (x axis). In this case, pulses reflected by the surfaces located inside the sample are split by the diffraction grating in x-direction so that interference maxima showing depthscan reflections are also split in x-direction that permits the simultaneous registration of reflections using a CCD array. Each reflective layer at depth $z_i$ will be obtain as a signal to map its location.

6. Producing a high dynamic range 2D (depth-transversal coordinate) interference image with a high resolution the interferometric system wherein the reference interferometer arm comprises a reflection mirror movable to the two different positions with a path difference more than grating time-display window ($T_d \leq 20$ ps) and a variable neutral-density filter. PZT stretched fiber can be inserted to create the delay time more than $T_d$. A signal arm comprises a convex cylindrical (spherical) lens or their combination, to create, for example, a linear source image on the surface of the sample, and registration system. Two images are obtained. A 2D imaging CCD array acquires two images sequentially with (signal) and without (reference) interference corresponding for two different positions of the reference mirror. These signal and reference images are computer subtracted to produce a 2D (depth-transversal coordinate) dark-field interference image.

7. Increasing the system sensitivity and dynamic range of the interferometric system of this invention one has a reference mirror moving by a PZT transducer into two positions with the path difference equal to $\lambda/2$, where $\lambda$ is the source central wavelength. The positions of the reference mirror are managed by a photodetector-PZT feedback loop to acquire two images one is background+signal and the other is background−signal corresponding for the two positions of the PZT. These two images are subtracted to produce a 2D (depth-transversal coordinate) dark-field interference image with double sensitivity. In this way the background is removed and signal is doubled. (Background+signal)−(background−signal)=2 signal.

8. Increasing the data acquisition speed and removing background the interferometric system is performed using a reference arm comprising a focusing lens, acousto-optical modulator (AOM), 90° reflection prism, two reflection mirrors placed against the prism reflection sides so that the beam deflected by the AOM and reflected by the one of the prism side and one of the mirrors is directed back to the diffraction grating at the diffraction angle−$\alpha$. CCD frames with and without interference are subtracted sequentially one from another to produce a series of the 2D (depth-transversal coordinate) dark-field interference images.

9. To perform optical tomography and histology or catheter-endoscope tomography the single-shot interferometric system is performed so that signal beam is scanning for example by a rotating mirror to illuminate a sample at different transverse positions. These signals are used to produce serial optical sections of narrow Z-depth for each transverse position which can then be rendered into 3-d image.

10. To increase the data acquisition speed, spatial resolution and signal to noise ratio the interferometric system includes a diffraction grating is moving along its plane with constant speed producing a Doppler shift frequency between signal and reference beams. The optical signal is detected by demodulating a multichannel linear array (LA) detector output at the Doppler shift frequency. In another version the diffraction grating is along its plane using, for example, a piezotransducer (PZT) so that grating displacement is more than the grating groove space.

11. Rotating the diffraction grating with constant angle speed to increase the tangential speed, DFS and the acquisition speed. In another version several diffraction gratings are disposed on the sides of the multisided cylindrical unit. These grating are rotated around the axes passing through the center and signal beam is discretely scanning in x (or y) direction so that position of each rotating grating is synchronized with a certain x (or y) position of the scanning system.

12. The use of diffraction grating carried on a cylindrical surface rotating with constant angle speed to increase the acquisition speed of the x (or y) scanning system and the lateral resolution.

13. To increase the axial resolution of the interferometer the interference image output is collected by a fiber linear array. Each fiber output is connected with a certain diode array pitch.

14. To simplify the multichannel photodetector LA and electronic detection system a diffraction grating and fiber linear array connected with a multichannel photodetector are placed against each other on a fast moving translator.

15. A diffraction grating comprising a composition of the several co-plane diffraction gratings with different spacing between grooves. When the central wavelength ($\lambda$) of the laser source is discretely tuned the position of the composition, the grating is discretely changed so that the groove space p satisfies the next relation p=$\lambda$/sin$\alpha$ (1), where ±$\alpha$ is the angle between reference (or signal) beams and normal to the diffraction grating.

Also, laser source is a linear array of the laser sources of different wavelengths $\lambda$ (400 to 600 nm). The laser source array is mounted on a holder, accommodating x (or y) translational stage allow to choose appropriate wavelength of the laser source.

16. To increase the sensitivity for the tissue imaging using short wavelength radiation at maximum tissue absorption wavelength the interferometric system uses laser sources adapted to emit at second harmonics.

17. The interferometric system as claimed in claims 7 to 11 wherein a vertical extension of the diffraction grating has a reflecting mirror. The diffracted beams are reflected from a stationary spherical mirror which displaces these beams in the vertical direction and directs them back to a rotating reflection mirror, Beams reflected from the rotating mirror are directed into a vertical slit. The slit plane is optically conjugated with the grating plane by the reflecting spherical mirror. Optical signal passing the slit is detected by demodulating the single detector output at the Doppler shift frequency between signal and reference beams produced by the rotating grating. This technique allows using a simple detection system.

18. To increase the data acquisition speed the interferometric system, beams reflected from a shaking (or rotation) grating are directed to a shaking (or rotation) reflection mirror placed at the axes of shaking (or rotation) of the grating and after mirror reflection are directed to a stationary fiber array connected to a multichannel photodetector.

19. To simplify the electronic detection, the interferometric system in a PZT shaking DG signal and reference beams are reflected from a small angle shaking reflection mirror. Beams reflected from the shaking mirror are directed into a vertical slit. Optical signal passing the slit is detected by demodulating the single detector output at the Doppler shift frequency.

20. To increase the SRR without additional diffraction gratings the diffraction grating is formed on the spherical (or cylindrical) reflection surface with a vertical extension reflecting mirror which is shaken over a small angle. The axes of the small angle shaking is passing through the center of the grating spherical (or cylindrical) reflection surface.

21. To get image of the sub structure of the human internal organ, mucous or tissue, for example an artery, the signal and reference interferometer arms are fiber-coupled. The input of the signal beam fiber is connected for example with a catheter and the fiber output is connected with a lens which directs the signal beam to the grating at a diffraction angle $\alpha$. The fiber output of the reference beam is connected with a lens which directs the reference beam to the grating at the diffraction angle $-\alpha$.

22. Using interferometric system as a receiver of a pulse code signal, retrieved from an optical memory system, for example, hole-burning holography. The pulse code signal is directed on the grating at the diffraction angle a and coherent reference pulse is directed on grating at the diffraction angle $-\alpha$.

23. Using the interferometric system as a receiver of a pulse code signal, received from optical communication system (OCS) The pulse code signal is directed on the grating at the angle diffraction a and coherent reference pulse extracted from OCS is directed on grating at the diffraction angle $-\alpha$.

24. An interferometric system having a signal beam which includes a zero-dispersion stretcher with moving slit placed in the stretcher spectral plane to measure dependence of the output signal position on the slit position. These measurements allow obtaining the spectral phase of the input pulse.

What is claimed is:

1. A system for performing selected optical measurements on a sample comprising:
   a. a broad band light source,
   b. means for splitting light from said light source into a signal beam and a reference beam,
   c. a reference mirror disposed along the path of the reference beam,
   d. means for bringing the signal beam to focus on said sample,
   e. a diffraction grating for receiving reflections from the sample and from the reference mirror, the reflections from the sample and the reference mirror being incident on the diffraction grating such that a diffraction order from each of said reflections propagate along a normal to said diffraction grating, the diffraction order from reflections from the sample being the same number as the diffraction order from reflections from the reference mirror, the diffraction order from one of said reflections being a positive order and the diffraction order from the other one of said reflections being a negative order,
   f. a detector,
   g. means for collecting the diffracted orders from said diffraction grating propagating along said normal and bringing said diffracted orders to focus on said detector, said detector producing an output of said diffracted orders received, and
   h. means for processing said output from said detector.

2. The system of claim 1 wherein the detector is a CCD array.

3. The system of claim 2 wherein the CCD array is a one-dimensional array.

4. The system of claim 1 wherein the reference mirror is stationary.

5. The system of claim 4 wherein the grating is stationary.

6. The system of claim 5 wherein the grating is a reflective-type grating.

7. The system of claim 1 wherein the broad band light source is a CPM laser.

8. The system of claim 1 wherein the processing means is a computer.

9. The system of claim 1 wherein the focusing means is a spherical lens.

10. The system of claim 1 wherein the light source is a Ti:sapphire laser.

11. The system of claim 1 wherein the detector is a 2D imaging CCD.

12. The system of claim 1 wherein the reflecting mirror is movable from a first position to a second position.

13. The system of claim 1 wherein the system further includes a demodulator coupled between the detector and the processing means, the detector is a multichannel diode array and the diffraction grating is movable.

14. The system of claim 13 wherein the light source is a laser.

15. The system of claim 14 wherein the system further includes means for shaking the diffraction grating.

16. The system of claim 14 wherein the system further includes means for rotating the diffraction grating.

17. The system of claim 16 wherein the diffraction grating is multisided.

18. The system of claim 14 wherein the system further includes a fiber linear array for transferring the diffraction orders from the collecting means to the detector.

19. The system of claim 17 and further including a fast moving translator and wherein said diffraction grating and one end of said fiber linear array are mounted on said fast moving translator.

20. A method for performing selected optical measurements on a sample according to this invention comprises:
   a. producing a beam of broad band light,
   b. splitting said beam of light into a signal beam and a reference beam,
   c. providing a reference mirror along the path of the reference beam,
   d. bringing the signal beam to focus on said sample,
   e. positioning a diffraction grating to receive reflections from the sample and from the reference mirror, the reflections being incident on the diffraction grating with respect to said diffraction grating normal such that a positive diffraction order from one of said reflections and a negative diffraction order form the other one of said reflections propagate along a normal to said diffraction grating, the two diffraction orders being the same number,
   f. providing a detector,
   g. collecting the diffracted orders from said diffraction grating propagating along said normal and bringing said diffracted orders collected to focus on said detector, said detector producing an output of said positive and negative diffracted orders received, and
   h. processing said output from said detector.

21. The method claim 20 wherein processing said output comprises forming an image map of a tissue substructure for GYN, GI, ADI tracts and/or bladder in-vivo and/or in-vitro in order to detect histological changes in tissue and artery wall such as plaque, fat and atheroscleroses.

22. The system of claim 1 wherein the means for bringing the signal beam to focus on said sample is a cylindrical lens.

23. The system of claim 11 wherein the system further includes the combination of a cylindrical lens for focusing the signal and reference beams into a narrow line on the surfaces of a grating and the 2D CCD array, and a scanning system to shift the narrow line along the 2D CCD array.

24. The system of claim 14 wherein the means for dividing light into a reference and a signal beam includes a lens to focus a reference and a signal beams onto a surface of the diffraction grating.

25. The system of claim 14 wherein the means for splitting light into a reference and a signal beam further includes a diffraction grating based zero-dispersion stretcher.

26. The system of claim 16 wherein the diffraction grating is cylindrical in shape.

27. The system of claim 16 wherein the diffraction grating is spherical in shape.

28. The system of claim 14 wherein the laser is a near infrared range laser such as $Cr^{4+}$: forsterite laser operated at from 1.1 to 1.3 $\mu$m, or a laser operated form 1.3 to 1.5 $\mu$m and amplified superluminescent diode operated from 0.8 to 1.5 $\mu$m.

29. The system of claim 14 wherein the means for bringing the signal beam to focus of said sample comprises a single mode fiber (SMF) inserted into a catheter-endoscope, the output surface of SMF comprises reflection coating, the beamsplitter connected to output to the SMF, fiber optics for bringing signal and reference beams into the diffraction grating, a fiber stretching piezotransduser, introducing optical delay equal the double optical distance between the output surface of SMF and the sample surface to produce an image map of substructure of GI tract, GYN tissue, bladder wall, artery, veins.

30. The system of claim 29 wherein the system further includes an acousto-optical modulator inserted into the signal beam or reference beam or both beams.

31. The method of claim 20 wherein positioning a moving diffraction grating such that one introduces a modulation frequency independent of source wavelength caused by interference of the positive and negative first, or second, or higher diffraction orders.

32. The method claim 31 wherein the detector output is demodulated, data is stored in a computer memory, processed by computer means and an image is produced of substructure of tissue at different depth below the surface.

33. The method fo claim 32 wherein processing includes converting said output from said detector to in vivo measure layer structure is a tissue and any changes in structure below the tissue surface.

34. The method of claim 33 wherein processing said output form said detector comprises converting Doppler frequency shift into the voltage to produce a blood flow map in a tissue, in arteries, and in veins.

35. The method of claim 33 wherein method further produces map of cancer regions, precancer regions, burns regions, plaque in arteries and other changes inside tissue from its normal histological state.

36. The method of claim 33 wherein method further produces histological map after application of varies chemicals treatment to evaluate cosmetics and drugs.

37. The system of claim 14 wherein a diffraction grating for receiving reflection from the sample is placed into the reference (or signal) beam, which is focused into a surface of the diffraction grating.

38. The system of claim 37 wherein a diffraction grating for receiving reflection from the sample is placed under the Bragg condition ($\alpha\beta$) so that diffracted beam is reflected opposite direction to the incident beam direction.

39. The system of claim 38 wherein a diffraction grating for receiving reflection from the sample or lenses, focusing beam into a surface of the diffraction grating are moved perpendicular to the direction of the incident beam to scan the tissue depth.

40. The system of claim 37 or 39 wherein the grooves of a diffraction grating for receiving reflection from the sample is radial.

41. The system of claim 40 wherein a diffraction grating with radial grooves is rotated relative to the center of the grating groove to produce modulation of the output.

42. A system for performing selected optical measurements on a sample comprising:
  a. a light source,
  b. a first beamsplitter for splitting light from said light source into a signal beam and a reference beam,
  c. a reference mirror disposed along the path of the reference beam,
  d. the sample being disposed along the path of the signal beam,
  e. a first lens for bringing the signal beam to focus on said sample,
  f. a diffraction grating for receiving reflections from the sample and from the reference mirror and producing therefrom a diffracted beam, the reflections from the sample and the reference mirror being incident on the diffraction grating such that a positive diffraction order from the reflections from one of the samples and reference mirror and a negative diffraction order from the reflections from the other one of the samples and reference mirror are directed along the same path,
  g. a detector,
  h. a second lens for bringing said positive diffraction order and said negative diffraction order which are directed along said same path to focus on said detector, said detector producing an output of said positive diffraction order and said negative diffraction order received, and
  i. a computer for processing said output form said detector.

43. A method for performing selected optical measurements on a sample comprising:
  a. providing a light source,
  b. splitting light from said light source into a signal beam and a reference beam,
  c. positioning a reference mirror along the path of the reference beam,
  d. positioning the sample along the path of the signal beam,
  e. bringing the signal beam to focus on said sample,
  f. positioning a diffraction grating for receiving reflections from the sample and from the reference mirror and producing therefrom a diffracted beam, the reflections from the sample and the reference mirror being incident on the diffraction grating such that a positive diffraction order from the reflections from one of the sample and reference mirror and a negative diffraction order from the reflections from the other one of the sample and reference mirror are directed along the same path, g. providing a detector, h. bringing said positive diffraction order and said negative diffraction order directed along said same path to focus on said detector, said detector producing an output of said positive diffraction order and said negative diffraction order received, and i. processing said output from said detector.

44. A system for performing selected optical measurements on a sample comprising:

a light source, b. a first beamsplitter for splitting light from said light source into a signal beam and a reference beam, c. a reference mirror disposed along the path of the reference beam, d. the sample being disposed along the paht of the signal beam, e. a first lens for bringing the signal beam to focus on said sample, f. a diffraction grating for receiving reflections from the reference mirror and producing therefrom a diffracted beam, the reflections from the reference mirror being incident on the diffraction grating such that a diffraction order from the reflections from the reference mirror is directed along a first path, g. a detector, h. a second beam-splitter for combing reflections from the sample with the diffraction order along said first path to produce a combined, beam, i. a second lens for bringing said combined beam to focus on said detector, said detector producing an output of said combined beam received, and j. a computer for processing said output from said detector.

45. The system of claim 42 wherein the diffraction order from reflections from the sample is the first diffraction order.

46. The system of claim 45 wherein the diffraction order form reflections from the reference mirror is the first diffraction order.

47. The system of claim 42 wherein the diffraction order from reflections from the sample is the second diffraction order.

48. The system of claim 47 wherein the diffraction order from reflections from the reference mirror is the second diffraction order.

49. The system of claim 42 wherein the diffraction order from reflections from the sample is a positive diffraction order and the diffraction order form the reference mirror is a negative diffraction order.

50. The system of claim 42 wherein said same path is normal to the diffraction grating.

51. The system of claim 42 wherein the light source is a broad band light source.

52. The system of claim 44 wherein the diffraction order from reflections from the reference mirror directed along said first path is a first order.

53. The system of claim 44 wherein the diffraction order from reflections from the reference mirror directed along said first path is a positive first order.

54. The system of claim 1 wherein the diffracted beam from the sample is a positive first order and the diffracted beam from the reference mirror is a negative first order.

* * * * *